(12) United States Patent
Audousset

(10) Patent No.: US 8,043,385 B2
(45) Date of Patent: Oct. 25, 2011

(54) COMPOSITION OXIDATION COLOURING OF KERATINIC FIBRES, CONTAINING A CATIONIC CELLULOSE ETHER, A METASILICATE AND OXIDATION DYES, METHOD FOR OXIDATION COLOURING AND USES THEREOF

(75) Inventor: Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/671,252

(22) PCT Filed: Jul. 17, 2008

(86) PCT No.: PCT/FR2008/051339
§ 371 (c)(1),
(2), (4) Date: Jun. 28, 2010

(87) PCT Pub. No.: WO2009/019383
PCT Pub. Date: Feb. 12, 2009

(65) Prior Publication Data
US 2010/0263138 A1     Oct. 21, 2010

Related U.S. Application Data

(60) Provisional application No. 60/935,741, filed on Aug. 29, 2007.

(30) Foreign Application Priority Data

Jul. 31, 2007  (FR) ..................................... 07 56856

(51) Int. Cl.
*A61Q 5/10*      (2006.01)
(52) U.S. Cl. ............. 8/405; 8/406; 8/408; 8/435; 8/552; 8/561; 8/562; 8/581

(58) Field of Classification Search ............... 8/405, 406, 8/408, 435, 552, 561, 562, 581
See application file for complete search history.

(56) References Cited

U.S. PATENT DOCUMENTS

| 7,399,319 | B2 | 7/2008 | Plos |
| 7,550,015 | B2 | 6/2009 | Legrand |
| 2005/0229330 | A1 | 10/2005 | Cottard et al. |

FOREIGN PATENT DOCUMENTS

| EP | 1 707 181 B1 | 10/2006 |
| EP | 1 747 774 A1 | 1/2007 |
| FR | 2 838 337 A1 | 10/2003 |
| WO | WO 2006/099163 A1 * | 9/2006 |

OTHER PUBLICATIONS

STIC Search Report dated Sep. 30, 2010.*
T.V. Drovetskaya et al., "Effects of low-level hydrophobic substitution on conditioning properties of cationic cellulosic polymers in shampoo systems," Journal of Cosmetic Science, vol. 55, No. Suppl., pp. 195-205 (2004).
International Search Report for PCT/FR2008/051339, dated May 18, 2009.

* cited by examiner

*Primary Examiner* — Eisa Elhilo
(74) *Attorney, Agent, or Firm* — Finnegan, Henderson, Farabow, Garrett & Dunner LLP

(57) ABSTRACT

The present invention relates to a dyeing composition comprising, in a medium appropriate for dyeing: A) one or more specific cationic cellulose ether (s), B) one or more metasilicate (s), and C) one or more benzene, heterocyclic or naphthalene oxidation dye (s). The present invention also relates to a method for dyeing keratinous fibers employing such a composition and to the use of this composition for dyeing of keratinous fibers.

39 Claims, No Drawings

1

COMPOSITION OXIDATION COLOURING OF KERATINIC FIBRES, CONTAINING A CATIONIC CELLULOSE ETHER, A METASILICATE AND OXIDATION DYES, METHOD FOR OXIDATION COLOURING AND USES THEREOF

CROSS REFERENCE TO RELATED APPLICATIONS

This application is a national phase application based on PCT/FR2008/051339, filed Jul. 17, 2008, which claims the priority of French Patent Application No. 0756856, filed Jul. 31, 2007; and claims the benefit of U.S. Provisional Application No. 60/935,741, filed Aug. 29, 2007, the contents of all of which are incorporated herein by reference.

A subject matter of the present invention is a composition for the oxidation dyeing of keratinous fibers, in particular human keratinous fibers, such as the hair, comprising one or more cationic cellulose ether(s), one or more metasilicate(s) and one or more benzene, heterocyclic or naphthalene oxidation dye(s).

Another subject matter of the invention is the use of this composition for the dyeing of keratinous fibers and the dyeing method employing this composition.

It is known to dye keratinous fibers, in particular human hair, with dyeing compositions comprising oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing products, can give rise, by an oxidative coupling process, to colored compounds.

It is also known that it is possible to vary the shades obtained with these oxidation bases by combining them with couplers or coloring modifiers, the latter being chosen in particular from aromatic meta-diamines, meta-aminophenols, meta-diphenols and certain heterocyclic compounds, such as indole compounds.

The variety of the molecules employed as oxidation bases and couplers makes it possible to obtain a rich palette of colors.

The "permanent" coloring obtained by virtue of these oxidation dyes furthermore has to satisfy a certain number of requirements. Thus, it must be without disadvantage toxicologically, it must make it possible to obtain shades within the desired intensity and it must behave well in the face of external agents, such as light, bad weather, washing, permanent waving, perspiration and rubbing.

The dyes must also make it possible to cover white hair and, finally, be as unselective as possible, that is to say make it possible to obtain the smallest possible differences in coloring along the same keratinous fiber, which generally comprises areas sensitized (i.e., damaged) to different extents from its tip to its root.

The use of cationic cellulose ethers in oxidation dyeing compositions for keratinous fibers is known, in particular through patent application WO 2006/099163.

The aim of the present invention is to obtain stable hair dyeing compositions, in particular in the form of creams, which are easy to prepare and to apply, which have good rheological qualities and which result in colorings which are relatively unselective and resistant to the various assaults to which keratinous fibers may be subjected.

The Applicant Company has discovered, surprisingly and advantageously, that the use, in combination, of one or more specific cationic cellulose ether(s), of one or more metasilicate(s) and of one or more dye(s) chosen from benzene, heterocyclic or naphthalene oxidation dyes makes it possible to obtain hair dyeing compositions of very good quality with improved properties.

The dyeing compositions according to the invention exhibit in particular the following properties:
these dyeing compositions can comprise dyes in the form of salts in high concentrations without exhibiting stability problems,
it is possible to obtain compositions having a viscosity corresponding to a cream which are stable over time,
these compositions are distinguished by an ease of mixing with the oxidizing composition,
these compositions are distinguished by the rheological qualities of the creams obtained (good cream viscosity as a mixture),
ease of application of the compositions after mixing with the oxidizing composition at the time of carrying out the dyeing (qualities of use on the head).

In addition, the compositions according to the invention make it possible to obtain compositions capable of resulting in colorings with varied, chromatic, powerful, attractive and relatively unselective shades which are uniform over the whole of the head of hair and which are highly resistant to the various assaults to which the fibers may be subjected.

These compositions are also nonaggressive to the scalp during application.

A subject matter of the present invention is a dyeing composition for keratinous fibers, in particular for human keratinous fibers, such as the hair, comprising, in a medium appropriate for dyeing, one or more specific cationic cellulose ether(s) described below, one or more metasilicate(s) and one or more oxidation dye(s) chosen from benzene, heterocyclic and naphthalene oxidation dyes.

Another subject matter of the present invention is a method for dyeing keratinous fibers in which the cosmetic composition according to the invention is employed.

A third subject matter of the invention relates to the use of this cosmetic composition for the dyeing of keratinous fibers, in particular human keratinous fibers, such as the hair.

Other characteristics, aspects, subject matters and advantages of the present invention will become even more clearly apparent on reading the description and examples which follow.

The dyeing composition for keratinous fibers according to the invention comprises, in a medium appropriate for dyeing:
A) one or more cationic cellulose ether(s) comprising from 4000 to 10 000 anhydroglucose units, said anhydroglucose units being substituted by at least:
(i) one substituent of formula $[R_4R_5R_6R_9N^+](X_2^-)$, in which:
$R_4$ and $R_5$ represent, independently of one another, a methyl or ethyl group,
$R_6$ represents a linear or branched $C_8$-$C_{24}$ alkyl group or an aralkyl group, the linear or branched alkyl part of which is a $C_8$-$C_{24}$ alkyl group,
$R_9$ represents a divalent group which makes possible the uniting with the anhydroglucose group and which is chosen from -(B)$_q$—CH$_2$—CHOH—CH$_2$— and —CH$_2$CH$_2$—,
q denoting 0 or 1,
B denoting a divalent group —(CH$_2$CH$_2$O)$_{n'}$—,
n' being an integer ranging from 1 to 100,
$X_2^-$ represents an anion; and
(ii) a substituent of formula $[R_1R_2R_3R_8N^+](X_1^-)$, in which:
$R_1$, $R_2$ and $R_3$ represent, independently of one another, a methyl or ethyl group, $R_8$ represents a divalent group which makes possible the uniting with the anhydroglucose group and which is chosen from $-(A)_p$-$CH_2$—CHOH—$CH_2$— and —$CH_2CH_2$—, p denoting 0 or 1, A denoting a divalent group —$(CH_2CH_2O)_n$—, n being an integer ranging from 1 to 100, $X_1^-$ represents an anion;

B) one or more metasilicate(s); and

C) one or more oxidation dye(s) chosen from benzene, heterocyclic and naphthalene oxidation dyes.

Preferably, the substituent (i) of formula $[R_4R_5R_6R_9N^+]$ $(X_2^-)$ is present in a mean of 0.0003 to 0.08 mol per mole of anhydroglucose unit.

The cationic cellulose ethers which can be used in the compositions of the invention are preferably hydroxy-ethyl or hydroxypropyl celluloses.

The cationic cellulose ethers which can be used in the compositions according to the invention preferably comprise more than 4500, advantageously more than 5000 and more preferably more than 6000 anhydroglucose units.

Preferably, the cationic cellulose ethers which can be used in the compositions according to the invention preferably comprise up to 9000 and preferably up to 8000 anhydroglucose units.

These cationic cellulose ethers and their process of preparation are described in application WO 2005/000903.

According to a preferred alternative form, the cationic cellulose ethers which can be used in the compositions according to the invention are formed of at least one unit (IV) and of at least one of the units (I), (II) or (III) below:

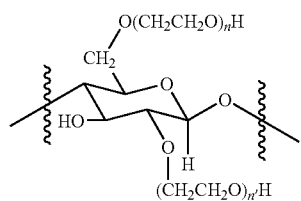
(I)

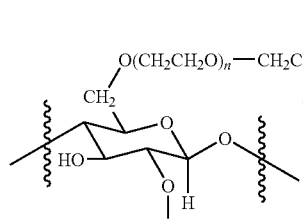
(II)

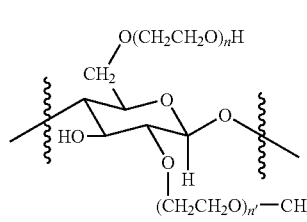
(III)

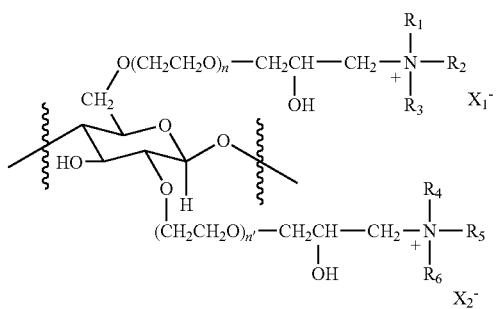
(IV)

with the proviso that:

the total number of the units (I)+(II)+(III)+(IV) is between 4000 and 10 000;

the ratio [(III)+(IV)]/[(I)+(II)+(III)+(IV)] ranges from 0.0003 to 0.8;

the ratio [(II)+(IV)]/[(I)+(II)+(III)+(IV)] ranges from 0.02 to 0.9;

the integers n and n' range, independently of one another, from 0 to 5;

$R_1$, $R_2$, $R_3$, $R_4$ and $R_5$ represent, independently of one another, a methyl or ethyl group;

$R_6$ represents a linear or branched $C_8$-$C_{24}$, preferably $C_{10}$-$C_{24}$, more preferably $C_{12}$-$C_{24}$ and better still $C_{12}$-$C_{15}$ alkyl group or an aralkyl group, the linear or branched alkyl part of which is a $C_8$-$C_{24}$ alkyl group;

$X_1^-$ and $X_2^-$ represent anions preferably chosen, independently of one another, from phosphate, nitrate, sulfate and halide ($Cl^-$, $Br^-$, $F^-$, $I^-$) ions.

According to a specific alternative form, the cationic cellulose ethers which can be used in the compositions according to the invention are formed of at least one unit (IV) and of at least one of the units (I), (II) or (III) above in which $R_6$ is a linear dodecyl group.

Mention may be made, among the cationic cellulose ethers which can be used in the compositions of the invention, of the polymers of Softcat SL-5, SL-30, SL-60 and SL-100 (INCI: Polyquaternium-67) type sold by Amerchol. The cationic cellulose ethers which are particularly preferred are the polymers of SL-60 and SL-100 type.

The composition according to the invention can comprise one or more cationic cellulose ether(s) as defined above.

The concentration of cationic cellulose ether(s) in the compositions according to the invention preferably ranges from 0.01 to 10% by weight, in particular from 0.05 to 3% by weight and more preferably from 0.1 to 1% by weight, with respect to the total weight of the composition.

The metasilicate(s) which can be used in the compositions of the invention preferably correspond(s) to the following general formula:

$$(Y^{p+})_n SiO_3^{2-}$$

in which:

Y denotes a mono- or divalent metal, preferably an alkali metal, such as, for example, Li, Na or K, or an alkaline earth metal, such as, for example, Ba, Mg or Ca, or an $NH_4$ group; n=1 or 2, p=1 or 2, and in particular, when n=1, then p=2 and, when n=2, then p=1.

Advantageously, the metasilicate according to the invention is sodium metasilicate $(Na^+)_2SiO_3^{2-}$.

The concentration of metasilicate(s) in the compositions according to the invention preferably ranges from 0.005 to 20% by weight, in particular from 0.1 to 10% by weight and more preferably from 0.2 to 5% by weight, with respect to the total weight of the composition.

The oxidation dye(s) which can be used according to the invention is (or are) chosen from benzene, heterocyclic and naphthalene oxidation dyes.

The oxidation dye(s) which can be used in the compositions of the invention can in particular be chosen from cationic or noncationic benzene bases, heterocyclic bases, benzene couplers, heterocyclic couplers and naphthalene couplers.

Preferably, the compositions according to the invention comprise one or more oxidation base(s).

The benzene oxidation bases can be cationic or noncationic.

Mention may be made, as noncationic benzene oxidation bases which can be used, of para-phenylenediamines, bisphenylalkylenediamines, para-aminophenols, ortho-aminophenols and their addition salts.

Mention may be made, among para-phenylenediamines of this type, by way of example, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylene-diamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine and their addition salts.

Among the para-phenylenediamines mentioned above, para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts are particularly preferred.

Mention may be made, among noncationic bisphenyl-alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylene-diamine, N,N'-bis(4-methylaminophenyl)tetramethylene-diamine, N,N'-bis(ethyl)-N,N'-bis(4'-amino-3'-methylphenyl) ethylenediamine, 1,8-bis(2,5-diaminophenoxy)-3,6-dioxaoctane and their addition salts.

Mention may be made, among noncationic para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol and their addition salts.

Mention may be made, among noncationic ortho-aminophenols, by way of example, of 2-aminophenol, 2-amino-5-methylphenol, 2-amino-6-methylphenol, 5-acetamido-2-aminophenol and their addition salts.

Mention may be made, as cationic benzene oxidation bases which can be used in the compositions according to the invention, of para-phenylenediamines, such as described in particular in patent applications FR-A-2 766 177 and FR-A-2 766 178, para-aminophenols, such as described, for example, in patent applications FR-A-2 766 177 and FR-A-2 766 178, ortho-phenylenediamines, such as described, for example, in patent applications FR-A-2 782 718, FR-A-2 782 716 and FR-A-2 782 719, ortho-aminophenols or double bases, such as derivatives of bis(aminophenyl)alkylenediamine type described in patent application FR-A-2 766 179, carrying at least one quaternary nitrogen atom.

Preferably, the cationic benzene oxidation bases which can be used in the compositions according to the invention are cationic para-phenylenediamines.

Advantageously, an alternative form consists in employing cationic oxidation bases with the para-phenylenediamine structure, at least one of the amine functional groups of which is a tertiary amine, carrier of a pyrrolidine ring, the molecule having at least one quaternized nitrogen atom. Such bases are, for example, described in the document EP-A-1 348 695.

According to one alternative form, the dyeing composition according to the invention comprises at least one cationic para-phenylenediamine chosen from the following compounds:

[1-(4-aminophenyl)pyrrolidin-3-yl]trimethylammonium chloride

[1-(4-aminophenyl)pyrrolidin-3-yl]dimethyltetradecylammonium bromide

3-[1-(4-aminophenyl)pyrrolidin-3-yl]-1-methyl-3H-imidazol-1-ium chloride

[1-(4-aminophenyl)pyrrolidin-3-yl](2-hydroxyethyl)dimethylammonium chloride

[1-(4-aminophenyl)pyrrolidin-3-yl]dimethyl(3-trimethylsilanylpropyl)ammonium chloride

[1-(4-aminophenyl)pyrrolidin-3-yl](3-trimethylammoniohexyl)dimethylammonium dichloride {2-[1-(4-aminophenyl)pyrrolidin-3-yloxy]ethyl}trimethylammonium chloride 1-{2-[1-(4-aminophenyl)pyrrolidin-3-yloxy]ethyl}-1-methylpyrrolidinium chloride 3-{3-[1-(4-aminophenyl)pyrrolidin-3-yloxy]propyl}-1-methyl-3H-imidazol-1-ium chloride 1-{2-[1-(4-aminophenyl)pyrrolidin-3-yloxy]ethyl}-1-methylpiperidinium chloride 3-{3-[1-(5-trimethylsilanylethyl-4-amino-3-(trimethylsilanylethyl)phenyl)pyrrolidin-3-yloxy]propyl}-1-methyl-3H-imidazol-1-ium chloride

[1-(4-amino-3-methylphenyl)pyrrolidin-3-yl]trimethylammonium chloride

[1-(4-amino-3-methylphenyl)pyrrolidin-3-yl]dimethyltetradecylammonium chloride

3-[1-(4-amino-3-methylphenyl)pyrrolidin-3-yl]-1-methyl-3H-imidazol-1-ium chloride

[1-(4-amino-3-methylphenyl)pyrrolidin-3-yl](2-hydroxyethyl)dimethylammonium chloride

[1-(4-amino-3-methylphenyl)pyrrolidin-3-yl]dimethyl (3-trimethylsilanylpropyl)ammonium chloride
[1-(4-amino-3-methylphenyl)pyrrolidin-3-yl] (3-tri-methylammoniohexyl)dimethylammonium dichloride
{2-[1-(4-amino-3-methylphenyl)pyrrolidin-3-yloxy] ethyl}trimethylammonium chloride
1-{2-[1-(4-amino-3-methylphenyl)pyrrolidin-3-yl-oxy] ethyl}-1-methylpyrrolidinium chloride
3-{3-[1-(4-amino-3-methylphenyl)pyrrolidin-3-yl-oxy]propyl}-1-methyl-3H-imidazol-1-ium chloride
1-{2-[1-(4-amino-3-methylphenyl)pyrrolidin-3-yl-oxy] ethyl}-1-methylpiperidinium chloride
[1-(4-amino-3-(trimethylsilanylethyl)phenyl)pyrrolidin-3-yl]trimethylammonium chloride
3-[1-(4-amino-3-(trimethylsilanylethyl)phenyl)pyrrolidin-3-yl]-1-methyl-3H-imidazol-1-ium chloride
3-{3-[1-(4-amino-3-(trimethylsilanylethyl)phenyl)-pyrrolidin-3-yloxy]propyl}-1-methyl-3H-imidazol-1-ium chloride
[1-(5-trimethylsilanylethyl-4-amino-3-(trimethylsilanylethyl)phenyl)pyrrolidin-3-yl]trimethylammonium chloride
3-[1-(5-trimethylsilanylethyl-4-amino-3-(trimethylsilanylethyl)phenyl)pyrrolidin-3-yl]-1-methyl-3H-imidazol-1-ium chloride
1'-(4-aminophenyl)-1-methyl-[1,3']bipyrrolidinyl-1-ium chloride
1'-(4-amino-3-methylphenyl)-1-methyl-[1,3']bipyrrolidinyl-1-ium chloride
3-{[1-(4-aminophenyl)pyrrolidin-3-ylcarbamoyl]-methyl}-1-methyl-3H-imidazol-1-ium chloride
3-{[1-(4-amino-3-methylphenyl)pyrrolidin-3-yl-carbamoyl]methyl}-1-methyl-3H-imidazol-1-ium chloride
3-[1-(4-aminophenyl)pyrrolidin-3-yl]-1-(3-trimethylsilanylpropyl)-3H-imidazol-1-ium chloride
3-[1-(4-aminophenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulfate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

"Heterocyclic base" or "heterocyclic oxidation base" is understood to mean, within the meaning of the present invention, any oxidation base comprising at least one heterocyclic group, other than a pyrrolidinyl group, the nitrogen atom of which is substituted by a para-aminophenyl group and which has at least one quaternized nitrogen atom.

Mention may be made, as heterocyclic oxidation bases which can be used in the compositions according to the invention, of pyridines, pyrimidines, pyrazoles, fused pyrazolopyrimidines, pyrazolotriazoles, pyrazolo-tetrazoles, pyrazolopyridazines, pyrazolothiazoles, pyrazoloimidazoles, pyrazolobenzimidazoles, pyrazolo-quinolines, aminopyrrolidines, aminopyrazolines, mono- or diaminotetraquinolines, diamino- or triamino-quinolines, aminoindazoles, diaminouracils, aminoindolenines, hydrazones, julolidine or lilolidine, and their derivatives and their addition salts.

Mention may be made, among pyridine derivatives, of the compounds described, for example, in patents GB-A-1 026 978 and GB-A-1 153 196, such as 2,5-diamino-pyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and their addition salts.

Other pyridine oxidation bases which can be used in the present invention are 3-aminopyrazolo[1,5-a]pyridines or their addition salts, for example described in patent application FR-A-2 801 308. Mention may be made, by way of example, of pyrazolo[1,5-a]pyridin-3-ylamine; 2-acetylaminopyrazolo[1,5-a]pyridin-3-ylamine; 2-(morpholin-4-yl) pyrazolo[1,5-a]pyridin-3-ylamine; 3-aminopyrazolo[1,5-a]pyridin-2-carboxylic acid; 2-methoxypyrazolo[1,5-a]pyridin-3-ylamine; (3-aminopyrazolo[1,5-a]pyridin-7-yl) methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diamino-pyrazolo[1,5-a]pyridine; 3,4-diaminopyrazolo[1,5-a]-pyridine, pyrazolo[1,5-a]pyridine-3,7-diamine; 7-(morpholin-4-yl) pyrazolo[1,5-a]pyridin-3-ylamine; pyrazolo[1,5-a]pyridin-3,5-diamine; 5-(morpholin-4-yl)pyrazolo[1,5-a]pyridin-3-ylamine; 2-[(3-amino-pyrazolo[1,5-a]pyridin-5-yl)(2-hydroxyethyl)-amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-amino-pyrazolo[1,5-a]pyridin-7-ol, and their addition salts.

Mention may be made, among pyrimidine derivatives, of the compounds described, for example, in patents DE-A-2359399; JP 88-169571; JP 05-63124; EP-A-0770375 or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in patent application FR-A-2 750 048, among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethyl-pyrazolo[1,5-a]pyrimidine-3,5-diamine; 3-amino-pyrazolo[1,5-a]pyrimidin-7-ol; 3-aminopyrazolo[1,5-a]-pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-amino-pyrazolo[1,5-a]pyrimidin-3-yl)(2-hydroxyethyl)amino]-ethanol, 5,6-dimethylpyrazolo[1,5-a]pyrimidine-3,7-di-amine, 2,6-dimethylpyrazolo[1,5-a]pyrimidine-3,7-di-amine, 2,5,N7,N7-tetramethylpyrazolo[1,5-a]pyrimidine-3,7-diamine, 3-amino-5-methyl-7-

(imidazolylpropyl-amino)pyrazolo[1,5-a]pyrimidine, their addition salts and their tautomeric forms, when a tautomeric equilibrium exists.

Mention may be made, among pyrazole derivatives, of the compounds described in patents DE-A-38 43 892, DE-A-41 33 957 and patent applications WO 94/08969, WO 94/08970, FR-A-2 733 749 and DE-A-195 43 988, such as 4,5-diamino-1-methylpyrazole, hydroxyethyl)pyrazole, 3,4-diaminopyrazole, 4,5-di-amino-1-(4'-chlorobenzyl)pyrazole, 4,5-di-amino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methyl-pyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)-pyrazole, 3,5-diamino-4-(β-hydroxyethyl)amino-1-methyl-pyrazole and their addition salts.

Mention may be made, as pyrazolotriazoles, of the compounds 3-amino-4-methyl-6-methylthio-2-phenyl-pyrazolo[3,2-c]-s-triazole, 3-amino-2,4,6-trimethyl-pyrazolo[3,2-c]-s-triazole or 3-amino-4,6-dimethyl-pyrazolo[3,2-c]-s-triazole. Such compounds are described in the document U.S. Pat. No. 5,457,200. Mention may also be made of the compounds 7-amino-2,6-dimethylpyrazolo[1,5-b][1,2,4]triazole, 7-amino-3,6-dimethylpyrazolo[3,2-c][1,2,4]triazole, 7-amino-3-methylpyrazolo[3,2-c][1,2,4]triazole, 7-amino-3-methyl-6-carboxypyrazolo[3,2-c][1,2,4]triazole, 7-amino-2-methylpyrazolo[1,5-b][1,2,4]triazole, 7-amino-2-phenyl-pyrazolo[1,5-b][1,2,4]triazole or 7-amino-2-methyl-6-carboxypyrazolo[1,5-b][1,2,4]triazole. These compounds are described in patent application EP-A-923 929.

Mention may be made, as pyrazolotetrazoles, of the compounds 7-amino-6-methylpyrazolo[1,5-e]tetrazole, 7-amino-6-phenylpyrazolo[1,5-e]tetrazole and 7-amino-6-carboxypyrazolo[1,5-e]tetrazole described in patent application EP-A-923 929.

Mention may be made, as pyrazolopyridazine, of 3-amino-pyrazolo[1,5-b]pyridazine. Such compounds are described in document U.S. Pat. No. 5,457,200.

Mention may be made, as pyrazolothiazoles, of the compounds 3-amino-2-methylpyrazolo[3,2-b]thiazole, 3-aminopyrazolo[3,2-b]thiazole and 3-amino-2,5-dimethyl-6-phenylpyrazolo[3,2-b]thiazole. Such compounds are described in the document U.S. Pat. No. 5,427,200.

Mention may be made, as pyrazoloimidazoles, of the compounds 3-amino-4-benzylpyrazolo[1,5-a]imidazole, 3-amino-2,4-dimethylpyrazolo[1,5-a]imidazole and 3-amino-4-methylpyrazolo[1,5-a]imidazole. Such compounds are described in the document U.S. Pat. No. 5,457,200. Mention may also be made of the compounds 7-amino-6-methylpyrazolo[1,5-a]imidazole, 7-aminopyrazolo[1,5-a]imidazole, 7-amino-2-methylpyrazolo[1,5-a]imidazole and 7-amino-2-phenylpyrazolo[1,5-a]imidazole described in patent application EP-A-923 929.

Mention may be made, as pyrazolobenzimidazoles, of the compounds 7-amino-6-methylpyrazolo[1,5-a]benzimidazole, 6,7-diaminopyrazolo[1,5-a]benzimidazole, 6,7-diamino-2-methylpyrazolo[1,5-a]benzimidazole and 6,7-diamino-2-phenylpyrazolo[1,5-a]benzimidazole described, for example, in patent application EP-A-923 929.

Mention may be made, as pyrazoloquinolines, of 3-amino-2-phenylpyrazolo[1,5-a]quinoline compounds. Such compounds are described in document U.S. Pat. No. 5,457,200.

Mention may be made, as aminopyrazolines, of the compounds 1-(4'-aminophenyl)-3-aminopyrazoline and 1-(4'-hydroxyphenyl)-3-aminopyrazoline. Such compounds are described in the document FR-A-2 018 056.

Mention may be made, as mono- or diaminotetrahydroquinolines, of the compounds 5-amino-1,2,3,4-tetra-hydroquinoline, 5-amino-7-chloro-8-piperidino-1,2,3,4-tetrahydroquinoline, 5-amino-7-chloro-8-morpholino-1,2,3,4-tetrahydroquinoline, 5,7-diamino-6-methyl-8-hydroxy-1,2,3,4-tetrahydroquinoline, 5-amino-8-methoxy-1,2,3,4-tetrahydroquinoline and 5-amino-7-chloro-8-dimethylamino-1,2,3,4-tetrahydroquinoline. Such compounds are described in the document DE-A-24 41 895.

Mention may be made, as diaminoquinolines, of the compounds 5,7-diamino-6-methyl-8-hydroxyquinoline and 5,7-diamino-2-methyl-8-hydroxyquinoline. Such compounds are described in the document DE-A-24 41 598.

Mention may be made, as triaminoquinolines, of 5,7-diamino-8-(methylamino)quinoline, 5,7-diamino-8-(dimethylamino)quinoline, 5,7-diamino-8-morpholino-quinoline, 5,7-diamino-8-[(β-hydroxyethyl)amino]-quinoline or 5,7,8-triaminoquinoline. Such compounds are described in the document DE-A-2441599.

Mention may be made, as aminoindazoles, of 4,7-diamino-5-methylindazole, 4,7-diamino-5,6-dimethylindazole, 6,7-diaminoindazole, 6-hydroxy-7-aminoindazole, 1-ethyl-6-hydroxy-7-aminoindazole, 6-aminoindazole or 5,6-diaminoindazole. Such compounds are described in the documents FR-A-2 315 906 and DE-A-14 92 166.

Mention may be made, as diaminouracils, of the compounds 5,6-diaminouracil, 5,6-diamino-2-thiouracil, 5,6-diamino-3-methyluracil, 5-amino-3-methyl-6-(methyl-amino)uracil, 5-amino-3-methyl-6-[(β-hydroxyethyl)-amino]uracil, 5-amino-3-methyl-6-(benzylamino)uracil, 5-amino-3-methyl-6-(phenylamino)uracil, 5,6-diamino-1-phenyluracil, 5,6-diamino-1,3-dimethyluracil, 5-amino-1,3-dimethyl-6-(methylamino)uracil, 5-amino-1,3-dimethyl-6-[(β-hydroxymethyl)amino]uracil, 5-amino-1,3-dimethyl-6-(benzylamino)uracil, 5-amino-1,3-dimethyl-6-(phenylamino)uracil and 5-amino-1,3-dimethyl-6-(dimethylamino)uracil. Such compounds are described in the document DE-A-25 33 629.

Mention may be made, as aminoindolenines, of the compounds 2-methyl-5-aminoindolenine and 1-(β-hydroxyethyl)-2-methyl-5-aminoindolenine. Such compounds are described in the document FR-A-1 602 547.

Mention may be made, as hydrazones, of the compounds N-methyl-4-pyridone hydrazone, N-methylthiazolone hydrazone, N-methyl-2-thiazolone hydrazone, N,N-dimethylbenzimidazolone hydrazone, N-methyl-2-pyridone hydrazone, N-methyl-2-benzothiazolone hydrazone, 1,2-dimethyl-3-indazolone hydrazone, 1,2,6-trimethyl-4-pyridone hydrazone, 1-methyl-2-quinolone hydrazone, 1,2,6-trimethyl-3-nitro-4-pyridone hydrazone, 1,2,6-trimethyl-3-amino-4-pyridone hydrazone, N-methylcyclohexenothiazolone hydrazone, 1,2,5-trimethyl-3-pyrazolone hydrazone, 1,2-dimethyl-3-indazolone hydrazone, 1,2-dimethyl-5-chloro-3-indazolone hydrazone, 1-methyl-2-ethyl-5-nitro-3-indazolone hydrazone, N-methyl-4-quinolone hydrazone and N-methyl-benzothiazolone 2-ω-benzenesulfonylhydrazone. Such compounds are described in the document FR-A-1 602 547.

Mention may be made, as julolidine or lilolidine derivatives, of the compounds 9-aminojulolidine, 9-amino-8-methyljulolidine, 9-amino-8,10-dimethyl-julolidine and 8-aminolilolidine. Such compounds are described in the document DE-A-24 41 597.

Preferably, the heterocyclic oxidation bases of use in the present invention are chosen from pyridines, pyrimidines, pyrazoles and pyrazolopyrimidines.

More preferably still, they are chosen from 4,5-diaminopyrazoles.

Particularly preferably, the benzene or heterocyclic oxidation bases used in the compositions according to the invention are chosen from cationic or noncationic para-phenylenediamines, cationic or noncationic para-aminophenols, pyrazole derivatives and their addition salts.

More preferably still, the oxidation bases used in the compositions according to the invention are chosen from pyrazole derivatives and their addition salts.

Mention may be made, as benzene couplers which can be used in the compositions according to the invention, of meta-aminophenols, meta-phenylenediamines, meta-diphenols and their addition salts.

The meta-aminophenols which can be used as benzene couplers in the dyeing compositions in accordance with the invention are preferably chosen from compounds of following formula (V):

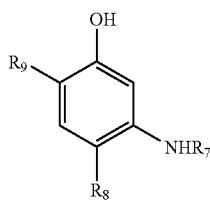

(V)

in which:

$R_7$ represents a hydrogen atom or a $C_1$-$C_4$ alkyl, $C_1$-$C_4$ monohydroxyalkyl or $C_2$-$C_4$ polyhydroxyalkyl group;

$R_8$ represents a hydrogen atom, a $C_1$-$C_4$ alkyl or $C_1$-$C_4$ alkoxyl group or a halogen atom chosen from chlorine, bromine or fluorine;

$R_9$ represents a hydrogen atom or a $C_1$-$C_4$ alkyl, $C_1$-$C_4$ alkoxyl, $C_1$-$C_4$ monohydroxyalkyl, $C_2$-$C_4$ polyhydroxyalkyl, $C_1$-$C_4$ monohydroxyalkoxyl or $C_2$-$C_4$ polyhydroxyalkoxyl group;

and from their addition salts.

Mention may more particularly be made, among the meta-aminophenols of formula (V) above, of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol and their addition salts.

The meta-phenylenediamines which can be used as benzene couplers in the dyeing composition in accordance with the invention are preferably chosen from compounds of following formula (VI):

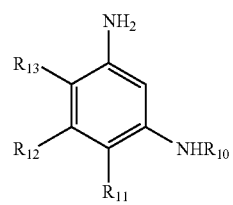

(VI)

in which:

$R_{10}$ represents a hydrogen atom or a $C_1$-$C_4$ alkyl, $C_1$-$C_4$ monohydroxyalkyl or $C_2$-$C_4$ polyhydroxyalkyl group;

$R_{11}$ and $R_{12}$, which are identical or different, represent a hydrogen atom or a $C_1$-$C_4$ alkyl, $C_1$-$C_4$ monohydroxyalkoxyl or $C_2$-$C_4$ polyhydroxyalkoxyl group;

$R_{13}$ represents a hydrogen atom, a $C_1$-$C_4$ alkoxyl, $C_1$-$C_4$ aminoalkoxyl, $C_1$-$C_4$ monohydroxyalkoxyl or $C_2$-$C_4$ poly-hydroxyalkoxyl group or a 2,4-diaminophenoxyalkoxyl group;

and from their addition salts.

Mention may more particularly be made, among the meta-phenylenediamines of formula (VI) above, of 2,4-di-aminobenzene, 3,5-diamino-1-ethyl-2-methoxybenzene, 3,5-di-amino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-(methylamino)benzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene and their addition salts.

The meta-diphenols which can be used as benzene couplers in the dyeing compositions in accordance with the invention are preferably chosen from compounds of following formula (VII):

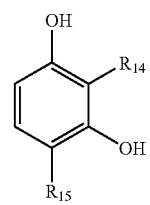

(VII)

in which:

$R_{14}$ and $R_{15}$, which are identical or different, represent a hydrogen atom, a $C_1$-$C_4$ alkyl group or a halogen atom chosen from chlorine, bromine or fluorine;

and from their addition salts.

Mention may more particularly be made, among the meta-diphenols of formula (VII) above, of 1,3-dihydroxy-benzene, 2-methyl-1,3-dihydroxybenzene, 4-chloro-1,3-dihydroxybenzene, 2-chloro-1,3-dihydroxybenzene and their addition salts.

Mention may be made, as heterocyclic couplers which can be used in the compositions according to the invention, of azole heterocyclic couplers, pyridine couplers, thiophenes, indolines, indoles, benzofurans, 8-amino-6-methoxyquinolines, 4-hydroxyquinolones, benzodioxoles, hydroxybenzamides, sesamol and its derivatives, benzo-morpholines and their addition salts.

The azole heterocyclic couplers used in the compositions according to the invention can be chosen in particular from carbazoles, hydroxyindazoles, benzoxazoles, pyrazoloazoles and pyrazolotriazoles, pyrroloazoles, imidazoloazoles, thiazoloazoles, pyrrolooxazoles, hydroxypyrazolopyrimidines, isoxazolones, indazolones and benzimidazoles.

Mention may be made, as carbazoles used in the compositions of the invention, of 1,3,6,8-tetramino-carbazole, 1,3,6,8-tetramino-9-(n-propyl)carbazole, 1,3,6,8-tetramino-9-(β-hydroxyethyl)carbazole, 1,3,6,8-tetramino-9-(2'-N,N-dimethylaminoethyl)-carbazole, and their addition salts. These compounds are described in application DE-A-27 15 680.

Mention may also be made, as carbazoles, of 3-aminocarbazole, described in application DE-A-277 496.

Mention may be made, as hydroxyindazoles preferably used in the compositions according to the invention, of the following monohydroxyindazoles: 4-hydroxyindazole, 5-hydroxyindazole, 6-hydroxyindazole, 7-hydroxy-indazole, 7-hydroxy-1-methylindazole, 4-hydroxy-6-methylindazole, 7-hydroxy-6-methylindazole, 7-hydroxy-4,6-dimethylindazole, 6-hydroxy-7-bromoindazole, 6-hydroxy-7-chloroindazole and 6-hydroxy-5,7-dichloro-indazole. These hydroxyindazoles are described in patent application DE-A-26 23 564.

Mention may be made, as benzoxazoles used in the compositions according to the invention, of the following diaminobenzoxazoles: 5,7-diaminobenzoxazole, 5,7-diamino-2-methylbenzoxazole, 5,7-diamino-2-ethyl-benzoxazole, 5,7-diamino-2-butylbenzoxazole, 5-dimethylamino-7-aminobenzoxazole, 5-amino-7-(diethyl-amino)benzoxazole and 4,6-diaminobenzoxazole. These benzoxazoles are described in patent application DE-A-27 19 424.

Mention may be made, as pyrazoloazoles used in the compositions according to the invention, of pyrazolo[1,5-b][1,2,4]triazoles, pyrazolo[3,2-c][1,2,4]triazoles, pyrazolotetrazoles, pyrazolo[1,5-a]imidazoles, pyrazolo[5,1-e]pyrazoles and pyrazolo[5,1-e][1,2,3]triazoles.

Preferably, the pyrazolo[1,5-b][1,2,4]triazoles are chosen from 2-methylpyrazolo[1,5-b][1,2,4]triazole, 2-ethylpyrazolo[1,5-b][1,2,4]triazole, 2-isopropyl-pyrazolo[1,5-b][1,2,4]triazole, 2-phenylpyrazolo[1,5-b][1,2,4]triazole, 2,6-dimethylpyrazolo[1,5-b][1,2,4]triazole, 6-methyl-2-ethylpyrazolo-[1,5-b][1,2,4]triazole, 6-methyl-2-isopropylpyrazolo[1,5-b][1,2,4]triazole, 6-methyl-2-phenylpyrazolo[1,5-b][1,2,4]triazole, 6-carboxy-2-methylpyrazolo[1,5-b][1,2,4]triazole, 6-carboxy-2-ethylpyrazolo[1,5-b][1,2,4]triazole, 6-carboxy-2-isopropylpyrazolo[1,5-b][1,2,4]triazole, 6-carboxy-2-phenylpyrazolo[1,5-b][1,2,4]triazole, 6-phenyl-2-methylpyrazolo[1,5-b][1,2,4]triazole, 6-phenyl-2-ethylpyrazolo[1,5-b][1,2,4]triazole, 6-phenyl-2-isopropylpyrazolo[1,5-b][1,2,4]triazole, 6-phenyl-2-phenylpyrazolo[1,5-b][1,2,4]triazole, 6-amino-2-methylpyrazolo[1,5-b][1,2,4]triazole, 6-amino-2-ethylpyrazolo[1,5-b][1,2,4]triazole, 6-amino-2-isopropylpyrazolo[1,5-b][1,2,4]triazole, 6-amino-2-phenylpyrazolo[1,5-b][1,2,4]triazole, 6-ethylthio-2-methylpyrazolo[1,5-b][1,2,4]triazole, 6-ethylthio-2-ethylpyrazolo[1,5-b][1,2,4]triazole, 6-ethylthio-2-isopropylpyrazolo[1,5-b][1,2,4]triazole, 6-ethylthio-2-phenylpyrazolo[1,5-b][1,2,4]triazole, 6-ethoxy-2-methylpyrazolo[1,5-b][1,2,4]triazole, 6-ethoxy-2-ethylpyrazolo[1,5-b][1,2,4]triazole, 6-ethoxy-2-isopropylpyrazolo[1,5-b][1,2,4]triazole, 6-ethoxy-2-phenylpyrazolo[1,5-b][1,2,4]triazole, 6-methyl-2-(2'-aminoethyl)pyrazolo-[1,5-b][1,2,4]triazole, 6-carboxy-2-(2'-aminoethyl)-pyrazolo[1,5-b][1,2,4]triazole, 6-phenyl-2-(2'-amino-ethyl)pyrazolo[1,5-b][1,2,4]triazole, 6-ethylthio-2-(2'-aminoethyl)pyrazolo[1,5-b][1,2,4]triazole, 2-(2'-aminoethyl)pyrazolo[1,5-b][1,2,4]triazole, 2-(2'-hydroxyethyl)pyrazolo[1,5-b][1,2,4]triazole, 6-methyl-2-(2'-hydroxyethyl)pyrazolo[1,5-b][1,2,4]triazole, 6-ethylthio-2-(2'-hydroxyethyl)pyrazolo[1,5-b][1,2,4]triazole, 6-carboxy-2-(2'-hydroxyethyl)-pyrazolo[1,5-b][1,2,4]triazole, 6-phenyl-2-(2'-hydroxy-ethyl)pyrazolo[1,5-b][1,2,4]triazole, 7-chloro-2,6-dimethylpyrazolo[1,5-b][1,2,4]triazole, 7-bromo-2,6-dimethylpyrazolo[1,5-b][1,2,4]triazole and their addition salts.

Preferably, the pyrazolo[3,2-c][1,2,4]triazoles are chosen from 3-methylpyrazolo[3,2-c][1,2,4]triazole, 3-methylsulfinyl-6-phenylpyrazolo[3,2-c][1,2,4]-triazole, 3-ethylpyrazolo[3,2-c][1,2,4]triazole, 3-isopropylpyrazolo[3,2-c][1,2,4]triazole, 3-phenylpyrazolo-[3,2-c][1,2,4]triazole, 3-(2'-aminoethyl)pyrazolo[3,2-c][1,2,4]triazole, 3-(2'-hydroxyethyl)pyrazolo[3,2-c][1,2,4]triazole, 6-methyl-3-ethylpyrazolo[3,2-c][1,2,4]triazole, 3,6-dimethylpyrazolo[3,2-c][1,2,4]-triazole, 6-methyl-3-isopropylpyrazolo[3,2-c][1,2,4]-triazole, 6-methyl-3-phenylpyrazolo[3,2-c][1,2,4]-triazole, 6-methyl-3-(2'-aminoethyl)pyrazolo[3,2-c][1,2,4]triazole, 6-methyl-3-(2'-hydroxyethyl)-pyrazolo[3,2-c][1,2,4]triazole, 6-methyl-3-methylthio-pyrazolo[3,2-c][1,2,4]triazole, 6-phenyl-3-methyl-pyrazolo[3,2-c][1,2,4]triazole, 6-phenyl-3-ethyl-pyrazolo[3,2-c][1,2,4]triazole, 6-isopropyl-3-ethyl-pyrazolo[3,2-c][1,2,4]triazole, 6-phenyl-3-isopropyl-pyrazolo[3,2-c][1,2,4]triazole, 6-phenyl-3-phenyl-pyrazolo[3,2-c][1,2,4]triazole, 6-phenyl-3-(2'-amino-ethyl)pyrazolo[3,2-c][1,2,4]triazole, 6-phenyl-3-(2'-hydroxyethyl)pyrazolo[3,2-c][1,2,4]triazole, 6-phenyl-3-methylthiopyrazolo[3,2-c][1,2,4]triazole, 6-ethyl-thio-3-methylpyrazolo[3,2-c][1,2,4]triazole, 6-ethyl-thio-3-ethylpyrazolo[3,2-c][1,2,4]triazole, 6-ethyl-thio-3-isopropylpyrazolo[3,2-c][1,2,4]triazole, 6-ethylthio-3-phenylpyrazolo[3,2-c][1,2,4]triazole, 6-ethylthio-3-(2'-aminoethyl)pyrazolo[3,2-c][1,2,4]-triazole, 6-ethylthio-3-(2'-hydroxyethyl)pyrazolo[3,2-c][1,2,4]triazole, 6-trifluoromethyl-3-methylthio-pyrazolo[3,2-c][1,2,4]triazole, 6-trifluoromethyl-pyrazolo[3,2-c][1,2,4]triazole, 6-carboxy-3-methyl-pyrazolo[3,2-c][1,2,4]triazole, 6-carboxy-3-ethyl-pyrazolo[3,2-c][1,2,4]triazole, 6-carboxy-3-isopropyl-pyrazolo[3,2-c][1,2,4]triazole, 6-carboxy-3-phenyl-pyrazolo[3,2-c][1,2,4]triazole, 6-carboxy-3-(2'-amino-ethyl)pyrazolo[3,2-c][1,2,4]triazole, 6-carboxy-3-(2'-hydroxyethyl)pyrazolo[3,2-c][1,2,4]triazole, 7-chloro-3,6-dimethylpyrazolo[3,2-c][1,2,4]triazole, 7-methoxy-carbonyl-3,6-dimethylpyrazolo[3,2-c][1,2,4]triazole, and their addition salts.

Preferably, the pyrazolotetrazoles are chosen from pyrazolo[5,1-e]tetrazole, 6-methylpyrazolo[5,1-e]tetrazole, 6-phenylpyrazolo[5,1-e]tetrazole, 6-carboxy-pyrazolo[5,1-e]tetrazole, 7-chloro-6-methylpyrazolo-[5,1-e]tetrazole and their addition salts.

Preferably, the pyrazolo[1,5-a]imidazoles are chosen from pyrazolo[1,5-a]imidazole, 2-methylpyrazolo[1,5-a]-imidazole, 2-phenylpyrazolo[1,5-a]imidazole, pyrazolo[1,5-a]benzimidazole, 6-methylpyrazolo[1,5-a]imidazole, 2,6-dimethylpyrazolo[1,5-a]imidazole, 6-methyl-2-phenylpyrazolo[1,5-a]imidazole, 6-methyl-pyrazolo[1,5-a]benzimidazole, 6-phenylpyrazolo[1,5-a]imidazole, 6-phenyl-2-methylpyrazolo[1,5-a]imidazole, 2,6-diphenylpyrazolo[1,5-a]imidazole, 6-phenylpyrazolo-[1,5-a]benzimidazole, 6-carboxypyrazolo[1,5-a]imidazole, 6-carboxy-2-methylpyrazolo[1,5-a]imidazole, 6-carboxy-2-phenylpyrazolo[1,5-a]imidazole, 6-carboxypyrazolo[1,5-a]benzimidazole, 6-ethoxypyrazolo

[1,5-a]imidazole, 6-ethoxy-2-methyl-pyrazolo[1,5-a]imidazole, 6-ethoxy-2-phenylpyrazolo-[1,5-a]imidazole, 6-trifluoromethylpyrazolo[1,5-a]benz-imidazole, 6-aminopyrazolo[1,5-a]imidazole, 6-amino-2-methylpyrazolo[1,5-a]imidazole, 6-amino-2-phenyl-pyrazolo[1,5-a]imidazole, 6-aminopyrazolo[1,5-a]benz-imidazole, 6-ethylthiopyrazolo[1,5-a]imidazole, 6-ethylthio-2-methylpyrazolo[1,5-a]imidazole, 6-ethyl-thio-2-phenylpyrazolo[1,5-a]imidazole, 7-chloro-6-methylpyrazolo[1,5-a]imidazole, 7-chloro-6-methyl-pyrazolo[1,5-a]benzimidazole and their addition salts.

Preferably, the pyrazolo[5,1-e]pyrazoles are chosen from 8-amino-4-methylpyrazolo[5,1-e]pyrazole, 8-amino-5-chloro-4-methylpyrazolo[5,1-e]pyrazole and their addition salts.

Preferably, the pyrazolo[5,1-e][1,2,3]triazoles are chosen from 5-methylpyrazolo[5,1-e][1,2,3]triazole, 5-methyl-6-chloropyrazolo[5,1-e][1,2,3]triazole, 5-phenylpyrazolo[5,1-e][1,2,3]triazole and their addition salts.

These pyrazoloazoles are described in patent application WO 97/35551.

Mention may be made, as pyrroloazoles used in the compositions according to the invention, of pyrrolo[1,2-b][1,2,4]triazoles, pyrrolo[2,1-c][1,2,4]-triazoles, pyrrolo[1,2-c]imidazoles, pyrrolo[1,2-e]-tetrazoles, pyrrolo[1,2-a]pyrroles, pyrrolo[1,2-a]imidazoles, pyrrolo[1,2-c][1,2,3]triazoles and their addition salts.

Preferably, the pyrrolo[1,2-b][1,2,4]triazoles are chosen from 3,4-dicyano-8-methylpyrrolo[1,2-b][1,2,4]-triazole, 3,4-dicyano-8-phenylpyrrolo[1,2-b][1,2,4]-triazole, 3,4-dicyano-8-(tert-butyl)pyrrolo[1,2-b][1,2,4]triazole, 5-chloro-3,4-dicyano-8-methyl-pyrrolo[1,2-b][1,2,4]triazole and 5-cyano-4-ethoxy-carbonyl-8-methylpyrrolo[1,2-b][1,2,4]triazole, 5-cyano-4-carboxy-8-methylpyrrolo[1,2-b][1,2,4]triazole, 4,5-dicyano-8-methylpyrrolo[1,2-b][1,2,4]triazole, 5-cyano-8-methyl-4-phenylpyrrolo[1,2-h][1, 2,4]triazole, 4,8-dimethylpyrrolo[1,2-h][1,2,4]triazole, 4,5-di(ethoxycarbonyl)-8-methylpyrrolo[1,2-h][1,2,4]triazole, 3-chloro-5-cyano-4-ethoxycarbonyl-8-methylpyrrolo[1,2-b][1,2,4]triazole, 5-cyano-4-ethoxycarbonyl-8-phenylpyrrolo[1,2-b][1,2,4]triazole, 5-cyano-4-carboxy-8-phenylpyrrolo[1,2-b][1,2,4]triazole, 4,5-dicyano-8-phenylpyrrolo[1,2-b][1,2,4]triazole, 4,5-di(ethoxycarbonyl)-8-phenylpyrrolo[1,2-b][1,2,4]triazole, 3-chloro-5-cyano-4-ethoxycarbonyl-8-phenylpyrrolo[1,2-b][1,2,4]triazole, 4-cyano-5-carboxy-8-(2-nitro-5-hydroxyphenyl)pyrrolo[1,2-b][1,2,4]triazole and their addition salts.

Preferably, the pyrrolo[2,1-c][1,2,4]triazoles are chosen from 5,6-dicyano-3-methylpyrrolo[2,1-c][1,2,4]-triazole, 7-chloro-5,6-dicyano-3-methylpyrrolo[2,1-c][1,2,4]triazole and 6,7-dicyano-3-methylpyrrolo[2,1-c][1,2,4]triazole, 5-chloro-6,7-dicyano-3-methyl-pyrrolo[2,1-c][1,2,4]triazole, 6,7-di(ethoxycarbonyl)-3-methylpyrrolo[2,1-c][1,2,4]triazole, 7-cyano-3-methyl-6-phenylpyrrolo[2,1-c][1,2,4]triazole, 7-cyano-3-methyl-6-(tert-butyl)pyrrolo[2,1-c][1,2,4]triazole and their addition salts.

Preferably, the pyrrolo[1,2-c]imidazoles are chosen from 6,8-dicyano-5-ethoxycarbonylpyrrolo[1,2-c]-imidazole, 4-chloro-6,8-dicyano-5-ethoxycarbonyl-pyrrolo[1,2-c]imidazole and their addition salts.

Preferably, the pyrrolo[1,2-e]tetrazoles are chosen from 6,7-dicyanopyrrolo[1,2-e]tetrazole, 6-cyano-7-ethoxycarbonylpyrrolo[1,2-e]tetrazole, 5-chloro-6,7-dicyanopyrrolo[1,2-e]tetrazole and their addition salts.

Preferably, the pyrrolo[1,2-a]imidazoles are chosen from 2,3,7-tricyano-6-methylpyrrolo[1,2-a]imidazole, 2,3,7-tricyano-6-trifluoromethylpyrrolo[1,2-a]imidazole, 2,3,7-tricyano-6-(tert-butyl)pyrrolo[1,2-a]imidazole, 2,3,7-tricyano-6-phenylpyrrolo[1,2-a]imidazole, 2,3,7-tricyano-6-ethoxycarbonylpyrolo-[1,2-a]imidazole, 5-chloro-2,3,7-tricyano-6-(tert-butyl)pyrrolo[1,2-a]imidazole, 5-chloro-2,3,7-tricyano-6-phenylpyrrolo[1,2-a]imidazole, 7-cyano-6-ethoxy-carbonylpyrrolo[1,2-a]benzimidazole, 7-cyano-6-phenyl-pyrrolo[1,2-a]benzimidazole, 7-amido-6-ethoxycarbonyl-pyrrolo[1,2-a]benzimidazole and their addition salts.

Preferably, the pyrrolo[1,2-c][1,2,3]triazoles are chosen from 5,6,8-tricyanopyrrolo[1,2-c][1,2,3]-triazole, 5,8-dicyano-6-ethoxycarbonylpyrrolo[1,2-c][1,2,3]triazole, 4-chloro-5,8-dicyano-6-ethoxy-carbonylpyrrolo[1,2-c][1,2,3]triazole and their addition salts.

These pyrroloazoles are described in patent application WO 97/35554.

Mention may be made, as imidazoloazoles used in the compositions according to the invention, of imidazolo[3,2-a]imidazoles, imidazolo[1,2-b][1,2,4]-triazoles and imidazolo[2,1-c][1,2,4]triazoles and their addition salts.

Preferably, the imidazolo[3,2-a]imidazoles are chosen from 7,8-dicyanoimidazolo[3,2-a]imidazole, 7,8-dicyano-4-methylimidazolo[3,2-a]imidazole, 7,8-dicyano-4-ethylimidazolo[3,2-a]imidazole, 7,8-dicyano-4-isopropylimidazolo[3,2-a]imidazole, 7,8-dicyano-4-phenylimidazolo[3,2-a]imidazole, 5-chloro-7,8-dicyano-4-methylimidazolo[3,2-a]imidazole, 7,8-dicyano-4-trifluoromethylimidazolo[3,2-a]imidazole and their addition salts.

Preferably, the imidazolo[1,2-b][1,2,4]triazoles are chosen from imidazolo[1,2-b][1,2,4]triazole, 6-methylimidazolo[1,2-b][1,2,4]triazole, 6-isopropylimidazolo-[1,2-b][1,2,4]triazole, 6-phenylimidazolo[1,2-b][1,2,4]triazole, 2,6-dimethylimidazolo[1,2-b][1,2,4]-triazole, 6-isopropyl-2-methylimidazolo[1,2-b][1,2,4]-triazole, 2-methyl-6-phenylimidazolo[1,2-b][1,2,4]-triazole, 6-methyl-2-phenylimidazolo[1,2-b][1,2,4]-triazole, 6-isopropyl-2-phenylimidazolo[1,2-b][1,2,4]-triazole, 7-chloro-2,6-dimethylimidazolo[1,2-b][1,2,4]-triazole, 7-chloro-2-phenyl-6-(tert-butyl)imidazolo-[1,2-b][1,2,4]triazole, 6-trifluoromethylimidazolo[1,2-b][1,2,4]triazole and their addition salts.

Preferably, the imidazolo[2,1-c][1,2,4]triazoles are chosen from imidazolo[2,1-c][1,2,4]triazole, 5-methyl-imidazolo[2,1-c][1,2,4]triazole, 5,8-dimethylimidazolo-[2,1-c][1,2,4]triazole, 5-methyl-8-phenylimidazolo[2,1-c][1,2,4]triazole, 8-phenylimidazolo[2,1-c][1,2,4]-triazole, 6-chloro-5,8-dimethylimidazolo[2,1-c][1,2,4]-triazole and their addition salts.

These imidazoloazoles are described in patent application WO 97/35552.

The thiazoloazoles are described in patent application FR-A-2 752 524.

Mention may be made, as pyrrolooxazoles used in the compositions according to the invention, of the compounds described generally in patent application FR-A-2 752 522 and their addition salts.

Mention may be made, as hydroxypyrazolopyrimidines used in the compositions according to the invention, of hydroxypyrazolo[1,5-a]pyrimidines and more particularly 2-hydroxy-5-methyl-7-ethylpyrazolo[1,5-a]pyrimidine, 2-hydroxy-5,6,7-trimethylpyrazolo[1,5-a]pyrimidine, 2-hydroxy-5,7-dimethyl-6-ethylpyrazolo[1,5-a]-pyrimidine, 2-hydroxy-7-methylpyrazolo[1,5-a]-pyrimidine, 2-hydroxy-5-methyl-7-carboxypyrazolo[1,5-a]pyrimidine, 2,7-dihydroxy-5,6-dimethylpyrazolo[1,5-a]pyrimidine and their addition salts. These hydroxy-pyrazolopyrimidines are described in patent application DE-A-40 29 324.

Mention may be made, as isoxazolones used in the compositions according to the invention, of 4-carboxy-β,γ-benzisoxazolone, 1-acetyl-4-carboxy-β,γ-benzisoxazolone, 6-carboxy-β,γ-benzisoxazolone, 1-acetyl-6-carboxy-β,γ-benzisoxazolone, β,γ-benzisoxazolone, 1-acetyl-β,γ-benzisoxazolone, 4-methyl-β,γ-benzisoxazolone, 1-acetyl-4-(β-hydroxy-ethylamino)carbonyl-β,γ-benzisoxazolone, 3-phenyl-isoxazol-5-one, 2-acetyl-3-phenylisoxazol-5-one, 3,4-diphenylisoxazol-5-one, 3-methylisoxazol-5-one, 3,4-tetramethyleneisoxazol-5-one and their addition salts.

These isoxazolones are described in patent application FR-A-2 040 260.

Mention may be made, as indazolones used in the compositions according to the invention, of indazolone, 5-chloroindazolone, 6-chloroindazolone, 1-ethylindazolone, 5-dimethylaminoindazolone, 1-methylindazolone, 1-isopropylindazolone, 1-butylindazolone, 3-chloroindazolone, 4-chloroindazolone, 5-methyl-indazolone, 6-methylindazolone, 5-ethyl indazolone, 6-propylindazolone, 5-butylindazolone, 1,5-dimethylindazolone, 1,6-dimethylindazolone, 1-methyl-5-chloroindazolone, 1-methyl-6-chloroindazolone, 1-ethyl-5-chloroindazolone, 1-ethyl-6-bromoindazolone, 5-aminoindazolone, 6-dimethylaminoindazolone, 5-diethylamino-indazolone, 1-methyl-5-dimethylaminoindazolone, 5-di-butylaminoindazolone, 1-ethyl-5-dipropylaminoindazolone and their addition salts.

These indazolones are described in patent application DE-A-26 32 390.

Mention may be made, as benzimidazoles used in the compositions according to the invention, of 4,7-di-hydroxybenzimidazole, 4,7-dihydroxy-1-methylbenzimidazole, 4,7-dihydroxy-2-methylbenzimidazole, 4,7-dihydroxy1-ethylbenzimidazole, 4,7-dihydroxy-1-propylbenzimidazole, 4,7-dihydroxy-1-butylbenzimidazole, 4,7-dihydroxy-2-ethylbenzimidazole, 4,7-dihydroxy-2-butylbenzimidazole, 4,7-dihydroxy-1,2-dimethylbenzimidazole, 4,7-dimethoxybenzimidazole, 4,7-dimethoxy-1-methylbenzimidazole, 4,7-dimethoxy-1-ethylbenzimidazole, 4,7-dimethoxy-2-methylbenzimidazole, 4,7-dimethoxy-2-ethylbenzimidazole, 5,6-dihydroxybenzimidazole, 5,6-dihydroxy-1-methylbenzimidazole, 5,6-dihydroxy-1-ethylbenzimidazole, 5,6-dihydroxy-1-butylbenzimidazole, 5,6-dihydroxy-2-methylbenzimidazole, 5,6-dihydroxy-2-butylbenzimidazole, 5,6-dihydroxy-2-phenylbenzimidazole, 5,6-dimethoxybenzimidazole, 5,6-dimethoxy-1-methylbenzimidazole, 5,6-dimethoxy-1-ethylbenzimidazole, 5,6-dimethoxy-1-propylbenzimidazole, 5,6-dimethoxy-2-methylbenzimidazole, 5,6-dimethoxy-2-butylbenzimidazole, 5,6-dimethoxy-2-phenylbenzimidazole, 5,6-dimethoxy-1,2-dimethylbenzimidazole, 4-hydroxy-7-methoxybenzimidazole, 5-hydroxy-6-methoxybenzimidazole, 4-hydroxy-7-methoxy-1-methylbenzimidazole, 5-hydroxy-6-methoxy-1,2-dimethylbenzimidazole. These benzimidazoles are described in patent application DE-A-28 12 678.

Mention may also be made, as benzimidazoles used in the compositions according to the invention, of ω-cyano-acetylbenzimidazoles, described generally in application DE-A-24 46 632, in particular 5-amino-1-methyl-2-(ω-cyanoacetyl)benzimidazole, and their addition salts.

Mention may be made, as pyridine couplers used in the compositions according to the invention, of 2-amino-3-hydroxypyridine, 2,3-diaminopyridines, 3-amino-5-hydroxypyridines and their addition salts.

Mention may be made, as 2,3-diaminopyridines used in the compositions according to the invention, of 6-methoxy-3-amino-2-(phenylamino)pyridine, 6-methoxy-3-amino-2-(4'-hydroxyphenyl)pyridine, 6-methoxy-3-amino-2-[(2'-methoxyphenyl)amino]pyridine, 6-methoxy-3-amino-2-[(2'-hydroxyphenyl)amino]pyridine, 6-methoxy-3-amino-2-(diethylamino)pyridine, 6-methoxy-3-amino-2-(dimethylamino)pyridine, 6-methoxy-3-amino-2-[methyl (2'-hydroxyethyl)amino]pyridine, 6-methoxy-3-amino-2-[(n-butyl)(2'-hydroxyethyl)amino]pyridine, 6-methoxy-3-amino-2-[bis(2'-hydroxyethyl)amino]pyridine, 6-methoxy-3-amino-2-[(2',3'-dihydroxypropyl)amino]pyridine, 6-methoxy-3-amino-2-[(1',1'-dimethyl-2'-hydroxy-ethyl)amino]pyridine, 6-methoxy-3-amino-2-[(1'-hydroxy-methyl-2'-hydroxyethyl)amino]pyridine, 6-methoxy-3-amino-2-[(1'-methyl-2'-hydroxyethyl)amino]pyridine, 6-methoxy-3-amino-2-[(3'-dimethylaminopropyl)amino]-pyridine, 6-methoxy-3-amino-2-[bis(methoxyethyl)amino]-pyridine, 6-methoxy-3-amino-2-[bis(2'-propenyl)amino]-pyridine, 6-methoxy-3-amino-2-pyrrolidinylpyridine, 6-methoxy-3-amino-2-(3'-acetamidopyrrolidinyl)pyridine, 6-methoxy-3-amino-2-(2',5'-dimethylpyrrolidinyl)-pyridine, 6-methoxy-3-amino-2-[(2'-dimethylamino-ethyl)amino]pyridine, 6-methoxy-3-amino-2-morpholino-pyridine, 6-methoxy-3-amino-2-(2'-methylpyrrolidinyl)-pyridine, 6-methoxy-3-amino-2-piperazinylpyridine, 6-methoxy-3-amino-2-pyridinylpyridine, 6-methoxy-3-amino-2-pyrrolidinylpyridine, 6-methoxy-3-amino-2-(2'-methylpyridinyl)pyridine, 6-methoxy-3-amino-2-(2'-(hydroxyethyl)pyridinyl)pyridine, 6-methoxy-3-amino-2-[(2'-pyrrolidinylethyl)amino]pyridine, 6-methoxy-3-amino-2-[(3'-imidazolinylpropyl)amino]pyridine, 6-methoxy-3-amino-2-[(3'-(3"-methylimidazolio)propyl)-amino]pyridine, 6-(2'trifluoroethoxy)-5-trifluoromethyl-2,3-diaminopyridine, 6-phenoxy-5-trifluoromethyl-2,3-diaminopyridine, 6-methoxy-2,3-diaminopyridine, and their addition salts.

Preferably, among the latter compounds, the pyridine coupler is chosen from the compounds 6-methoxy-3-amino-2-(hydroxyethylamino)pyridine, 6-methoxy-3-amino-2-[(2',3'-dihydroxypropyl)amino]pyridine, 6-methoxy-3-amino-2-[(1'-methyl-2'-hydroxyethyl)amino]pyridine, 6-methoxy-3-amino-2-pyrrolidinylpyridine, 6-methoxy-3-amino-2-(2'-methylpyrrolidinyl)pyridine, 6-methoxy-3-amino-2-(2'-methylpyridinyl)pyridine, 6-methoxy-3-amino-2-(2'-(hydroxyethyl)pyridinyl)pyridine, 6-methoxy-2,3-diaminopyridine and their addition salts.

These couplers can be prepared according to known methods described in the literature. Reference may be made, by way of examples, to patent application DE-A-32 33 540.

Mention may be made, as 3-amino-5-hydroxypyridines used in the compositions according to the invention, of 3-amino-5-hydroxy-2,6-dimethoxypyridine, 3-amino-5-hydroxy-2,6-di(2'-hydroxyethyloxy)pyridine and their addition salts. These 3-amino-5-hydroxypyridines are described in patent application DE-A-34 42 128.

Use will preferably be made, as pyridine couplers, of 2-amino-3-hydroxypyridine and its addition salts.

Mention may be made, as thiophenes used in the compositions according to the invention, of ω-cyano-acetylthiophenes, described generally in application DE-A-24 46 632, in particular 5-amino-2-(ω-cyano-acetyl)thiophene, and their addition salts.

Mention may be made, as indolines used in the compositions according to the invention, of 5-amino-indolines 6-aminoindolines, 7-aminoindolines, 4-hydroxyindoline, 5-hydroxyindoline, 6-hydroxyindoline, 5,6-dihydroxyindoline, 5,6-diaminoindoline and 5,7-diaminoindoline, 5-amino-6-nitroindoline, 5-bromo-7-nitroindoline, 6-nitroindoline, and their addition salts, in particular their hydrochlorides. These indolines are described in patent U.S. Pat. No. 4,013,404.

Mention may be made, among 5,7-diaminoindolines, of: 5,7-diamino-1-methylindoline, 5,7-diamino-2-methylindoline, 5,7-diamino-3-methylindoline, 5,7-diamino-2,2-dimethylindoline, 5,7-diamino-2,3-dimethylindoline, 5,7-diamino-2-methyl-3-ethylindoline, 5,7-diamino-1-ethyl-2-methyl-2-ethylindoline, 5,7-diamino-6-methylindoline, 5,7-diamino-1,6-dimethylindoline, 5-dimethylamino-7-amino-1-butylindoline, 5-diethylamino-7-amino-2,2-dipropylindoline, 5-amino-7-dimethylamino-2-methyl-3-butylindoline, 5-amino-7-dibutylamino-3,3-diethylaminoindoline, 5,7-bis(dimethylamino)indoline and their addition salts. These indolines are described in patent application DE-A-27 16 671.

Mention may also be made of the following indolines and their salts: 6-aminoindoline, 6-hydroxyindoline, 1-ethyl-6-aminoindoline or 1-N-ethyl-4-hydroxyindoline. These indolines are described in patent application DE-A-19 16 139.

Mention may be made, among 5,6-dihydroxyindolines, of: 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and 2-carboxy-5,6-dihydroxyindoline, and their addition salts. These indolines are described in patent application WO 01/93818.

Mention may be made, as indoles used in the compositions according to the invention, of 6-hydroxy-indole and its derivatives, 5,6-dihydroxyindole and its derivatives, 4-hydroxyindole and its derivatives, and their addition salts. Preferably, the indole coupler is 6-hydroxyindole.

Mention may be made, as benzofurans used in the compositions according to the invention, of hydroxy-benzofurans, diaminobenzofurans and ω-cyanoacetylbenzofurans, and their addition salts.

Preferably, the hydroxybenzofurans used are 2-methyl-6-hydroxybenzofuran, 3-methyl-6-hydroxybenzofuran, 2,4-dimethyl-6-hydroxybenzofuran, 3-(n-propyl)-6-hydroxybenzofuran, 2-ethyl-5-hydroxybenzofuran, 2-methyl-5-hydroxybenzofuran, 3-methyl-5-hydroxybenzofuran, 3-isobutyl-5-hydroxybenzofuran, 3-ethyl-5-hydroxybenzofuran, 2,6-dimethyl-5-hydroxybenzofuran, 3,6-dimethyl-5-hydroxybenzofuran, 6,7-dimethyl-5-hydroxybenzofuran, 3-(n-propyl)-5-hydroxybenzofuran, 3-methyl-4-(n-propyl)-5-hydroxybenzofuran, 2-hexyl-5-hydroxybenzofuran, 2-(n-propyl)-5-hydroxybenzofuran, 4-(tert-butyl)-5-hydroxybenzofuran, 6-(tert-butyl)-5-hydroxybenzofuran, 4-methyl-5-hydroxybenzofuran, 3-methyl-5-(n-propyl)-4-hydroxybenzofuran, 2-ethyl-4-hydroxybenzofuran, 2-methyl-6-pentyl-4-hydroxybenzofuran, 6-pentyl-4-hydroxybenzofuran, 3,5-dimethyl-4-hydroxybenzofuran, 3,7-dimethyl-4-hydroxybenzofuran, 2,6-di(tert-butyl)-4-hydroxybenzofuran, 2-methyl-4-hydroxybenzofuran, 3-methyl-4-hydroxybenzofuran, 2-methyl-7-ethyl-4-hydroxybenzofuran, 2,7-dimethyl-4-hydroxybenzofuran, 2-isopropyl-4-hydroxybenzofuran, 3-ethyl-4-hydroxybenzofuran, 3-methyl-7-(tert-butyl)-4-hydroxybenzofuran, 3-methyl-5-(tert-butyl)-4-hydroxybenzofuran, 2,6-dimethyl-4-hydroxybenzofuran, 3-iso-propyl-4-hydroxybenzofuran, 3-(n-propyl)-4-hydroxybenzofuran, 3-methyl-7-(n-propyl)-4-hydroxybenzofuran, 3-methyl-6-(n-propyl)-7-hydroxybenzofuran, 3-methyl-7-hydroxybenzofuran, 2-ethyl-4-methyl-7-hydroxybenzofuran, 2-ethyl-5-methyl-7-hydroxybenzofuran, and their addition salts. These hydroxybenzofurans are described in patent application EP-A-0 506 549.

Preferably, the diaminobenzofurans used are 5,7-diaminobenzofuran, 5,7-diamino-2-methylbenzofuran, 5,7-diamino-2-ethylbenzofuran, 5-dimethylamino-7-aminobenzofuran, 4,6-diaminobenzofuran and their addition salts. These diaminobenzofurans are described in patent application DE-A-27 19 424.

Preferably, the ω-cyanoacetylbenzofurans used are ω-cyanoacetylbenzofurans, described generally in application DE-A-24 46 632, in particular 5-amino-2-(ω-cyanoacetyl)benzofuran, and their addition salts.

Mention may be made, as 8-amino-6-methoxyquinolines used in the compositions according to the invention, of 8-amino-6-methoxyquinoline, 8-amino-5-bromo-6-methoxyquinoline, 8-amino-5-chloro-6-methoxyquinoline, 8-amino-5,7-dibromo-6-methoxyquinoline, 8-amino-5-methyl-6-methoxyquinoline, 8-amino-5,7-dimethyl-6-methoxyquinoline, 8-amino-5-ethyl-6-methoxyquinoline, 8-amino-5-butyl-6-methoxyquinoline, 8-amino-5-phenyl-6-methoxyquinoline, 8-amino-2-phenyl-6-methoxyquinoline, 8-amino-2-benzyloxy-6-methoxyquinoline, 8-amino-4-dimethylamino-6-methoxyquinoline, 8,4-diamino-6-methoxyquinoline, 8-amino-4-chloro-6-methoxyquinoline, and their addition salts. These 8-amino-6-methoxyquinolines are described in patent application DE-A-26 26 141.

Mention may be made, as 4-hydroxyquinolones used in the compositions according to the invention, of 7-dimethylamino-4-hydroxy-2-quinolone, 6-methyl-4-hydroxy-2-quinolone, 6-dimethylamino-4-hydroxy-2-quinolone, 6-methoxy-4-hydroxy-2-quinolone, 8-chloro-4-hydroxy-2-quinolone, 1-methyl-7-dimethylamino-4-hydroxy-2-quinolone, 1-methyl-4-hydroxy-2-quinolone, 1-methyl-8-chloro-4-hydroxy-2-quinolone, 1,6-dimethyl-4-hydroxy-2-quinolone, 1-methyl-6-dimethylamino-4-hydroxy-2-quinolone, 6-(2-hydroxyethyl)-4-hydroxy-2-quinolone, 1-isopropyl-4-hydroxy-2-quinolone, 1-methyl-7-isopropyl-4-hydroxy-2-quinolone, 1-(n-butyl)-8-bromo-4-hydroxy-2-quinolone, and their addition salts. These 4-hydroxyquinolones are described in patent application DE-A-23 34 738.

Mention may be made, as benzodioxoles used in the compositions according to the invention, of the compounds described generally in patent applications DE-A-197 18 534 and DE-A-28 13 076.

Preferably, the benzodioxoles used are 5-amino-1,3-benzodioxole, 5-hydroxy-1,3-benzodioxole, 5-amino-2-methyl-1,3-benzodioxole, 5-hydroxy-2,2-dimethyl-1,3-benzodioxole, 5-hydroxy-2-ethyl-1,3-benzodioxole, 5-hydroxy-2-butyl-1,3-benzodioxole, 5-hydroxy-2-phenyl-1,3-benzodioxole, 5,6-dihydroxy-1,3-benzodioxole, 4,7-dihydroxy-1,3-benzodioxole, 4,7-diamino-2-methyl-1,3-benzodioxole, 5,6-diamino-2,2-diphenyl-1,3-benzodioxole, 4,5,7-triamino-1,3-benzodioxole, 5-hydroxy-7-methyl-2,2-diethyl-1,3-benzodioxole, and their addition salts with an acid, which are described in patent application DE-A-28 13 076.

Mention may be made, as hydroxybenzamides used in the compositions according to the invention, of 2,4-di-hydroxybenzamides and in particular N-phenyl-2,4-di-hydroxybenzamide, N-(2'-methoxyphenyl)-2,4-dihydroxybenzamide, N-(3'-methoxyphenyl)-2,4-dihydroxybenzamide, N-(4'-methoxyphenyl)-2,4-dihydroxybenzamide, N-(4'-carboxyphenyl)-2,4-dihydroxybenzamide, N-(2'-pyridyl)-2,4-dihydroxybenzamide, N-(3'-pyridyl)-2,4-dihydroxybenzamide, N-(2',5'-dimethoxyphenyl)-2,4-dihydroxybenzamide, N-(3',5'-dimethoxyphenyl)-2,4-dihydroxybenzamide, N-(2'-methoxy-5'-aminophenyl)-2,4-dihydroxybenzamide, N-(4'-(N,N-dimethylamino)phenyl)-2,4-dihydroxybenzamide, N-(4'-hydroxyphenyl)-2,4-dihydroxybenzamide, N-methyl-2,4-dihydroxybenzamide, N-benzyl-2,4-dihydroxybenzamide, unsubstituted 2,4-dihydroxybenzamide and their addition salts. These hydroxybenzamides are described in patent application DE-A-38 22 449.

Mention may be made, as sesamol derivatives used in the compositions according to the invention, in addition to sesamol, of 1-N-β-hydroxyethylamino-3,4-methylenedioxybenzene.

Mention may be made, as benzomorpholines used in the compositions according to the invention, of 6-hydroxybenzomorpholine and 6-aminobenzomorpholine, and their addition salts.

Mention may be made, as naphthalene coupler(s) which can be used in the compositions according to the invention, of α-naphthol, substituted naphthalenes of following formula (VIII), and their addition salts:

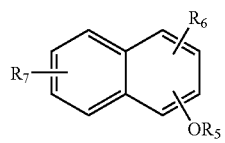

in which:
$R_5$ represents a hydrogen atom or a —CO—R group in which R represents a $C_1$-$C_4$ alkyl group;
$R_6$ represents a hydrogen atom, a hydroxyl group, a $C_1$-$C_4$ alkyl group or an —$SO_3H$ group;
$R_7$ represents a hydrogen atom or a hydroxyl group;
it being understood that at least one of the $R_5$ to $R_7$ groups is other than a hydrogen atom.

Mention may in particular be made, among naphthalene couplers which can preferably be used in the dyeing compositions in accordance with the invention, of:
α-naphthol,
1,7-dihydroxynaphthalene,
2,7-dihydroxynaphthalene,
2,5-dihydroxynaphthalene,
2,3-dihydroxynaphthalene,
1-acetoxy-2-methylnaphthalene,
1-hydroxy-2-methylnaphthalene,
1-hydroxy-4-naphthalenesulfonic acid,
and their addition salts.

Particularly preferably, the oxidation couplers used in the compositions according to the invention are chosen from meta-aminophenols, meta-phenylenediamines, meta-diphenols, indolines and indoles, and their addition salts.

Preferably, the oxidation dye(s) of the invention is (or are) chosen from benzene or heterocyclic oxidation dyes.

The oxidation bases and oxidation couplers can be present in the compositions of the invention in the form of addition salts and in particular in the form of addition salts with an acid.

The addition salts with an acid which can be used in the context of the invention are chosen in particular from hydrochlorides, hydrobromides, sulfates, citrates, succinates, tartrates, lactates, acetates, alkyl sulfates and alkylsulfonates.

When the oxidation bases or the oxidation couplers comprise one or more carboxylic or sulfonic acid functional groups, the addition salts with a base can be envisaged.

The addition salts with a base which can be used in the context of the dyeing compositions of the invention are then in particular those obtained with sodium hydroxide, potassium hydroxide, aqueous ammonia or amines.

The concentration of oxidation dye(s) in the compositions according to the invention preferably ranges from 0.005 to 15% by weight, in particular from 0.01 to 10% by weight and more preferably from 0.5 to 5% by weight, with respect to the total weight of the composition.

The dyeing composition in accordance with the invention can additionally comprise one or more direct dye(s) which can be chosen in particular from nitrobenzene dyes, azo direct dyes, methine direct dyes and their addition salts. These direct dyes can be nonionic, anionic or cationic in nature.

The medium used in the compositions according to the present invention is an aqueous medium or a medium comprising water and at least one organic solvent.

The organic solvent(s) used in the compositions according to the present invention can be chosen from monohydroxylated alcohols and polyols.

Mention may be made, as monohydroxylated alcohols which can be used, of lower $C_1$-$C_4$ alcohols, such as ethanol, isopropanol, tert-butanol, n-butanol and their mixtures. Preferably, the alcohol used is ethanol.

Mention may be made, as polyols which can be used, of propylene glycol, polyethylene glycols, polyol ethers, such as 2-butoxyethanol, propylene glycol monomethyl ether, diethylene glycol monoethyl ether and diethylene glycol monomethyl ether, and aromatic alcohols, such as benzyl alcohol or phenoxyethanol, and their mixtures.

The concentration of organic solvent(s) in the compositions according to the present invention is preferably between 0 and 30% by weight and more preferably between 0 and 20% by weight, with respect to the total weight of the composition.

The dyeing composition in accordance with the invention can also comprise one or more adjuvant(s) conventionally used in hair dyeing compositions, such as anionic, cationic, nonionic, amphoteric or zwitterionic surface-active agents or their mixtures; nonionic, amphoteric, zwitterionic, anionic or additional cationic polymers, other than the cationic cellulose ethers according to the invention, or their mixtures; penetration agents; sequestering agents; fragrances; buffers; dispersing agents; conditioning agents, such as, for example, volatile or nonvolatile and modified or unmodified silicones; film-forming agents; ceramides; preservatives; opacifying agents; vitamins, amino acids; oligopeptides; peptides; hydrolyzed or nonhydrolyzed and modified or unmodified proteins; enzymes; branched or unbranched fatty acids and alcohols; animal, vegetable or mineral waxes; hydroxylated organic acids; UV screening agents; anti-oxidants and agents for combating free radicals; anti-dandruff agents; seborrhea-regulating agents; soothing agents; mineral, vegetable or animal oils; polyisobutenes and poly(α-olefin)s; pigments; acids; bases; plasticizers; inorganic fillers, pearlescent agents; glitter; antistatic agents and reducing agents.

The above adjuvant(s) is (or are) generally present in an amount of, for each of them, preferably between 0.01 and 40% by weight and more preferably between 0.1 and 25% by weight, with respect to the weight of the composition.

The compositions according to the present patent application can also comprise, as additional cosmetic adjuvant, at least one thickening agent, also known as "rheology-adjusting agent".

The rheology-adjusting agent (or agents) can be chosen from inorganic or organic thickening agents and in particular polymeric associative thickeners, additional fatty alcohols, other than the glycerolated surfactants according to the invention, (oleyl alcohol), additional cellulose derivatives, other than the cationic cellulose ethers according to the invention, (hydroxy-ethylcellulose, hydroxypropylcellulose or carboxy-methylcellulose) and gums of microbial origin (xanthan gum or scleroglucan gum).

The preferred rheology-adjusting agent (or agents) is (or are) chosen from fatty alcohols, nonionic cellulose ethers and gums of microbial origin.

The concentration of thickening agent(s) is preferably between 0.01 and 20% by weight and more preferably between 1 and 10% by weight, with respect to the total weight of the composition.

Of course, a person skilled in the art will take care to choose this (or these) optional additional compound(s) so that the advantageous properties intrinsically attached to the oxidation dyeing composition in accordance with the invention are not, or not substantially, detrimentally affected by the envisaged addition(s).

The pH of the dyeing composition in accordance with the invention generally ranges from 3 to 12 approximately and preferably between 5 and 11 approximately. It can be adjusted to the desired value using the metasilicate(s) according to the invention, optionally in combination with (an)other acidifying or basifying agent(s) commonly used in the dyeing of keratinous fibers, or else using conventional buffer system(s).

Mention may be made, among acidifying agents, by way of example, of inorganic or organic acids, such as hydrochloric acid, orthophosphoric acid, sulfuric acid, sulfonic acids and carboxylic acids, such as acetic acid, tartaric acid, citric acid and lactic acid.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of following formula (IX):

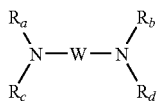

(IX)

in which:
W is a propylene residue optionally substituted by a hydroxyl group or a $C_1$-$C_4$ alkyl group;
$R_a$, $R_b$, $R_c$ and $R_d$, which are identical or different, represent a hydrogen atom or a $C_1$-$C_4$ alkyl or a $C_1$-$C_4$ hydroxyalkyl group.

The dyeing composition according to the invention can be provided in various forms, such as in the form of creams or gels or in any other form appropriate for carrying out dyeing of keratinous fibers, in particular of human hair.

The method for dyeing keratinous fibers of the present invention is a method in which the composition according to the present invention as defined above is applied to the fibers, preferably in the presence of at least one oxidizing agent, for a time sufficient to develop the desired color. The color can be developed at acidic, neutral or alkaline pH and the oxidizing agent (or agents) can be added to the composition of the invention only at the time of use or it (they) can be employed starting from an oxidizing composition comprising it (them), applied simultaneously with or sequentially to the composition of the invention.

According to a specific embodiment, the composition according to the present invention is a ready-for-use composition mixed, preferably at the time of use, with a composition comprising, in a medium appropriate for dyeing, at least one oxidizing agent, this oxidizing agent (or these oxidizing agents) being present in an amount sufficient to develop a coloring. The mixture obtained is subsequently applied to the keratinous fibers. After a leave-in time of 3 to 50 minutes approximately, preferably 5 to 30 minutes approximately, the keratinous fibers are rinsed, washed with shampoo, rinsed again and then dried.

The oxidizing agents conventionally used for the oxidation dyeing of keratinous fibers are, for example, hydrogen peroxide, urea hydrogen peroxide, alkali metal bromates, persalts, such as perborates and persulfates, peracids and oxidase enzymes, among which may be mentioned peroxidases, 2-electron oxidoreductases, such as uricases, and 4-electron oxygenases, such as laccases, these oxidoreductases optionally being combined with their usual cofactors, such as uric acid for uricases. The preferred oxidizing agent is hydrogen peroxide.

The oxidizing composition can also include various adjuvants conventionally used in compositions for dyeing the hair, such as defined above.

The pH of the oxidizing composition including oxidizing agent is such that, after mixing with the dyeing composition, the pH of the resulting composition applied to the keratinous fibers preferably varies from 3 to 12 approximately and preferentially from 5 to 10. It can be adjusted to the desired value using (an) acidifying or basifying agent(s) commonly used in the dyeing of keratinous fibers, such as defined above.

The ready-for-use composition which is finally applied to the keratinous fibers can be provided in various forms, such as in the form of creams or gels or in any other form appropriate for carrying out dyeing of keratinous fibers and in particular of human keratinous fibers, such as the hair.

Another subject matter of the invention is a dyeing kit or multicompartment device comprising at least one first compartment comprising the dyeing composition defined above and at least one second compartment comprising an oxidizing composition. This device can be equipped with a means allowing the desired mixture to be deposited on the hair, such as the devices described in patent application FR-A-2 586 913.

The examples which follow serve to illustrate the invention without, however, exhibiting a limiting nature.

EXAMPLES

The following compositions were prepared.

|  | Composition 1 | Composition 2 |
|---|---|---|
| 1-Methyl-2,5-diaminobenzene | 1.7 g | 0.5 g |
| 1-Hydroxy-4-aminobenzene | — | 0.4 g |
| 1,3-Dihydroxybenzene | 1 g | 0.25 g |
| 1-Hydroxy-3-aminobenzene | 0.07 g | — |
| 1-β-Hydroxyethyloxy-2,4-diaminobenzene dihydrochloride | 0.03 g | — |
| 2-Methyl-1,3-dihydroxybenzene | 0.5 g | 0.3 g |
| 1-Methyl-2-hydroxy-4-aminobenzene | — | 0.25 g |
| 1-Methyl-2-hydroxy-4-[β-hydroxyethylamino]benzene | — | 0.05 g |
| 6-Hydroxyindole | — | 0.01 g |
| Sodium metasilicate | 2 g | 1 g |
| Pure monoethanolamine | 5.7 g | 0.7 g |
| Aqueous ammonia solution at 20% by weight | — | 4 g |
| Cationic cellulose ether (Softcat SL-60, sold by Amerchol) | 0.2 g | 0.5 g |

|  | Composition 1 | Composition 2 |
|---|---|---|
| $C_{20}$-$C_{22}$ alcohols (Nafol 2022 EN, sold by Sasol) | 3 g | 3 g |
| Oleyl alcohol | 0.5 g | 0.5 g |
| Lauric acid monoethanolamide | 3 g | 3 g |
| Oxyethylenated stearyl alcohol comprising 2 mol of ethylene oxide | 5 g | 5 g |
| Oxyethylenated stearyl alcohol comprising 21 mol of ethylene oxide | 3.8 g | 3.8 g |
| Oleic acid | 3 g | 3 g |
| Aqueous solution comprising 60% by weight of hexadimethrine chloride (Mexomere 90, sold by Chimex) | 2 g | 2 g |
| Aqueous solution comprising 40% by weight of polyquaternium-6 (Merquat 100, sold by Ondeo) | 4 g | 4 g |
| $TiO_2$ | 0.2 g | 0.2 g |
| Reducing agent, anti-oxidant, sequestering agent, fragrance | q.s. | q.s. |
| Demineralized water, q.s. for | 100 g | 100 g |

Application Protocol

Each composition is diluted at the time of use with one and a half times its weight of 9-volume aqueous hydrogen peroxide solution (i.e., 2.7% by weight of $H_2O_2$) (pH in the vicinity of 3) for composition 1 and 20-volume aqueous hydrogen peroxide solution (i.e., 6% by weight of $H_2O_2$) (pH in the vicinity of 3) for composition 2. The mixture thus produced is a cream with a good consistency which is easy to apply to gray hair, comprising 90% of white hairs, in a proportion of 10 g per 1 g of hair, for 20 minutes. The hair is subsequently easily rinsed, washed with a standard shampoo and dried.

The hair coloring is evaluated visually. The results obtained with regard to natural gray hair, comprising 90% of white hairs, after treatment are as follows:

|  | Shade |
|---|---|
| Composition 1 | Natural chestnut |
| Composition 2 | Mahogany coppery dark blonde |

These colorings have good properties, in particular in terms of selectivity and persistence. They also have a good intensity. The compositions obtained are stable over time.

The following compositions were also prepared:

|  | Composition 3 | Composition 4 |
|---|---|---|
| 1-Methyl-2,5-diaminobenzene | — | 2 g |
| 2-(4,5-Diamino-1H-pyrazol-1-yl)ethanol hydrochloride | 2.15 g | — |
| 1-Hydroxy-3-aminobenzene | 1.1 g | 0.5 g |
| N,N-bis(2-hydroxyethyl)-para-phenylenediamine sulfate monohydrate | — | 0.4 g |
| 1,3-Dihydroxybenzene | — | 1.2 g |
| 1-(β-Hydroxyethyloxy)-2,4-diaminobenzene dihydrochloride | — | 0.6 g |
| 6-Hydroxybenzomorpholine | — | 0.15 g |
| Sodium metasilicate | 2 g | 1 g |
| Pure monoethanolamine | 5.7 g | 5.92 g |
| Aqueous solution of ammonia at 20% by weight | — | 4 g |
| Cationic cellulose ether (Softcat SL-100, sold by Amerchol) | 0.2 g | 0.1 g |
| $C_{20}$-$C_{22}$ alcohols (Nafol 2022 EN, sold by Sasol) | 3 g | 3 g |
| Oleyl alcohol | 0.5 g | 0.5 g |
| Lauric acid monoethanolamide | 2 g | 2 g |
| Oxyethylenated stearyl alcohol comprising 2 mol of ethylene oxide | 5 g | 5 g |
| Oxyethylenated stearyl alcohol comprising 21 mol of ethylene oxide | 3.8 g | 3.8 g |
| Oleic acid | 3 g | 3 g |
| Aqueous solution comprising 60% by weight of hexadimethrine chloride (Mexomere PO, sold by Chimex) | 2 g | 2 g |
| Aqueous solution comprising 40% by weight of polyquaternium-6 (Merquat 100, sold by Ondeo) | 2 g | 2 g |
| $TiO_2$ | 0.2 g | 0.2 g |
| Hydroxypropylmethylcellulose | 0.2 g | 0.1 g |
| Carbomer (Carbopol 980, sold by Noveon) | — | 0.3 g |
| Reducing agent, anti-oxidant, sequestering agent, fragrance | q.s. | q.s. |
| Demineralized water, q.s. for | 100 g | 100 g |

Application Protocol

Each composition is diluted at the time of use with one and a half times its weight of 9-volume aqueous hydrogen peroxide solution (pH in the vicinity of 3) for composition 3 and 20-volume aqueous hydrogen peroxide solution (pH in the vicinity of 3) for composition 4. The mixture thus produced is a cream with a good consistency which is easy to apply to gray hair, comprising 90% of white hairs, in a proportion of 10 g per 1 g of hair, for 20 minutes. The hair is subsequently easily rinsed, washed with a standard shampoo and dried.

The hair coloring is evaluated visually. The results obtained with regard to natural gray hair, comprising 90% of white hairs, after treatment are as follows:

|  | Shade |
|---|---|
| Composition 3 | Intense red |
| Composition 4 | Natural black |

These colorings have good properties, in particular in terms of selectivity and persistence. They also have a good intensity. The compositions obtained are stable over time.

What is claimed is:

1. A dyeing composition for keratinous fibers comprising, in a medium appropriate for dyeing:
A) one or more cationic cellulose ether(s) comprising from 4,000 to 10,000 anhydroglucose units, said anhydroglucose units being substituted by at least:
(i) one substituent of formula $[R_4R_5R_6R_9N^+](X_2^-)$, in which:

$R_4$ and $R_5$ represent, independently of one another, a methyl or ethyl group, $R_6$ represents a linear or branched $C_8$-$C_{24}$ alkyl group or an aralkyl group, the linear or branched alkyl part of which is a $C_8$-$C_{24}$ alkyl group, $R_9$ represents a divalent group which makes possible the uniting with the anhydroglucose group and which is chosen from -(B)$_q$—CH$_2$—CHOH—CH$_2$— and —CH$_2$CH$_2$—, q denoting 0 or 1, B denoting a divalent group —(CH$_2$CH$_2$O)$_{n'}$—, n' being an integer ranging from 1 to 100, $X_2^-$ represents an anion; and (ii) a substituent of formula $[R_1R_2R_3R_8N^+](X_1^-)$, in which:

$R_1$, $R_2$ and $R_3$ represent, independently of one another, a methyl or ethyl group, $R_8$ represents a divalent group which makes possible the uniting with the anhydroglucose group and which is chosen from -(A)$_p$-CH$_2$—CHOH—CH$_2$— and —CH$_2$CH$_2$—, p denoting 0 or 1, A denoting a divalent group —(CH$_2$CH$_2$O)$_n$—, n being an integer ranging from 1 to 100, $X_1^-$ represents an anion;

B) one or more metasilicate(s); and

C) one or more oxidation dye(s) chosen from benzene, heterocyclic, and naphthalene oxidation dyes.

2. The dyeing composition as claimed in claim 1, characterized in that the cationic cellulose ether is formed of at least one unit (IV) and of at least one of the units (I), (II), and (III) below:

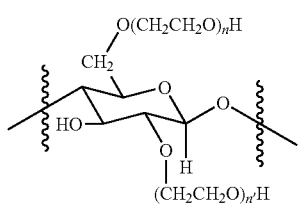
(I)

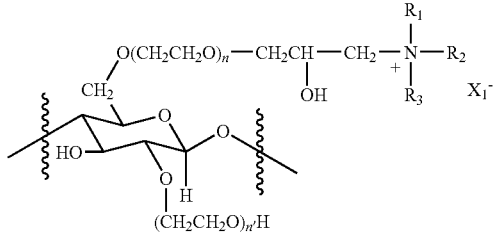
(II)

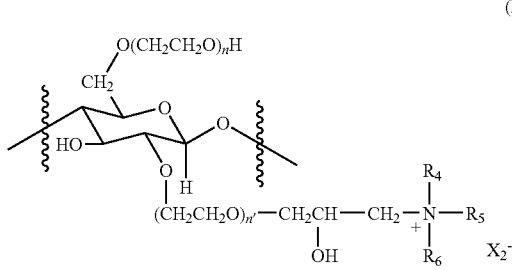
(III)

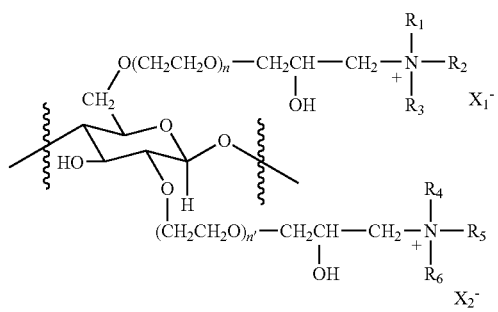
(IV)

with the proviso that:
the total number of the units (I)+(II)+(III)+(IV) is between 4,000 to 10,000;
the ratio of the numbers of units [(III)+(IV)]/[(I)+(II)+(III)+(IV)] ranges from 0.0003 to 0.8;
the ratio of the numbers of units [(II)+(IV)]/[(I)+(II)+(III)+(IV)] ranges from 0.02 to 0.9;
the integers n and n' range, independently of one another, from 0 to 5;
$R_1$, $R_2$, $R_3$, $R_4$ and $R_5$ represent, independently of one another, a methyl or ethyl group;
$R_6$ represents a linear or branched $C_8$-$C_{24}$ alkyl group or an aralkyl group, the linear or branched alkyl part of which is a $C_8$-$C_{24}$ alkyl group; and
$X_1^-$ and $X_2^-$ represent anions.

3. The dyeing composition as claimed in claim 2, characterized in that the $R_6$ represents a linear or branched alkyl group comprising from 12 to 15 carbon atoms.

4. The dyeing composition as claimed in one of claims 1 to 3, characterized in that the concentration of cationic cellulose ether(s) ranges from 0.01 to 10% by weight, with respect to the total weight of the composition.

5. The dyeing composition as claimed in one of claims 1 to 3, characterized in that the metasilicate corresponds to the following general formula:

$(Y^{p+})_n SiO_3^{2-}$ in which:
Y denotes a mono- or divalent metal, an alkaline earth metal, an NH$_4$ group; and
n=1 or 2, p=1 or 2.

6. The dyeing composition as claimed in one of claims 1 to 3, characterized in that the metasilicate is a sodium metasilicate.

7. The dyeing composition as claimed in one of claims 1 to 3, characterized in that the concentration of metasilicate(s) ranges from 0.005 to 20% by weight, with respect to the total weight of the composition.

8. The dyeing composition as claimed in one of claims 1 to 3, characterized in that the oxidation dye is chosen from cationic or noncationic benzene bases, heterocyclic bases, benzene couplers, heterocyclic couplers, and naphthalene couplers.

9. The dyeing composition as claimed in claim 8, characterized in that the oxidation dye is a benzene oxidation base chosen from para-phenylenediamines, bisphenylalkylenediamines, para-aminophenols, ortho-aminophenols, and their addition salts.

10. The dyeing composition as claimed in claim 9, characterized in that the benzene oxidation base is a para-phenylenediamine chosen from para-phenylenediamine, para-toluylenediamine, 2-chloro-para-phenylenediamine, 2,3- dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,62 -hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine, and their addition salts.

11. The dyeing composition as claimed in claim 9, characterized in that the benzene oxidation base is a bisphenylalkylenediamine chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(p-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts.

12. The dyeing composition as claimed in claim 9, characterized in that the benzene oxidation base is a para-aminophenol chosen from para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol, and their addition salts.

13. The dyeing composition as claimed in claim 9, characterized in that the benzene oxidation base is an ortho-aminophenol chosen from 2-aminophenol, 2-amino-5-methylphenol, 2-amino-6-methylphenol, 5-acetamido-2-aminophenol, and their addition salts.

14. The dyeing composition as claimed in claim 8, characterized in that the oxidation dye is a benzene oxidation base chosen from cationic para-phenylenediamines, cationic para-aminophenols, cationic ortho-phenylenediamines, cationic ortho-aminophenols, and cationic double bases of the family of the bis(aminophenyl)alkylenediamines, carrying at least one quaternary nitrogen atom.

15. The dyeing composition as claimed in claim 14, characterized in that the benzene oxidation base is a cationic para-phenylenediamine, at least one of the amine functional groups of which is a tertiary amine, carrier of a pyrrolidine ring, or para-phenylenediamine molecule having at least one quaternized nitrogen atom.

16. The dyeing composition as claimed in claim 14, characterized in that the cationic para-phenylenediamine is chosen from the following compounds:

[1-(4-aminophenyl)pyrrolidin-3-yl]trimethylammonium chloride,
[1-(4-aminophenyl)pyrrolidin-3-yl]dimethyltetradecylammonium bromide,
3-[1-(4-aminophenyl)pyrrolidin-3-yl]-1-methyl-3H-imidazol-1-ium chloride,
[1-(4-aminophenyl)pyrrolidin-3-yl](2-hydroxyethyl)dimethylammonium chloride,
[1-(4-aminophenyl)pyrrolidin-3-yl]dimethyl(3-trimethylsilanylpropyl)ammonium chloride,
[1-(4-aminophenyl)pyrrolidin-3-yl](3-trimethylammoniohexyl)dimethylammonium dichloride,
{2-[1-(4-aminophenyl)pyrrolidin-3-yloxy]ethyl}trimethylammonium chloride,
1-{2-[1-(4-aminophenyl)pyrrolidin-3-yloxy]ethyl}-1-methylpyrrolidinium chloride,
3-{3-[1-(4-aminophenyl)pyrrolidin-3-yloxy]propyl}-1-methyl-3H-imidazol-1-ium chloride,
1-{2-[1-(4-aminophenyl)pyrrolidin-3-yloxy]ethyl}-1-methylpiperidinium chloride,
3-{3-[1-(5-trimethylsilanylethyl-4-amino-3-(trimethylsilanylethyl)phenyl)pyrrolidin-3-yloxy]propyl}-1-methyl-3H-imidazol-1-ium chloride,
[1-(4-amino-3-methylphenyl)pyrrolidin-3-yl]trimethylammonium chloride,
[1-(4-amino-3-methylphenyl)pyrrolidin-3-yl]dimethyltetradecylammonium chloride,
3-[1-(4-amino-3-methylphenyl)pyrrolidin-3-yl]-1-methyl-3H-imidazol-1-ium chloride,
[1-(4-amino-3-methylphenyl)pyrrolidin-3-yl](2-hydroxyethyl)dimethylammonium chloride,
[1-(4-amino-3-methylphenyl)pyrrolidin-3-yl]dimethyl(3-trimethylsilanylpropyl)ammonium chloride,
[1-(4-amino-3-methylphenyl)pyrrolidin-3-yl](3-trimethylammoniohexyl)dimethylammonium dichloride,
{2-[1-(4-amino-3-methylphenyl)pyrrolidin-3-yloxy]ethyl}trimethylammonium chloride,
1-{2-[1-(4-amino-3-methylphenyl)pyrrolidin-3-yloxy]ethyl}-1-methylpyrrolidinium chloride,
3-{3-[1-(4-amino-3-methylphenyl)pyrrolidin-3-yloxy]propyl}-1-methyl-3H-imidazol-1-ium chloride,
1-{2-[1-(4-amino-3-methylphenyl)pyrrolidin-3-yloxy]ethyl}-1-methylpiperidinium chloride,
[1-(4-amino-3-(trimethylsilanylethyl)phenyl)pyrrolidin-3-yl]trimethylammonium chloride,
3-[1-(4-amino-3-(trimethylsilanylethyl)phenyl)pyrrolidin-3-yl]-1-methyl-3H-imidazol-1-ium chloride,
3-{3-[1-(4-amino-3-(trimethylsilanylethyl)phenyl)pyrrolidin-3-yloxy]propyl}-1-methyl-3H-imidazol-1-ium chloride,
[1-(5-trimethylsilanylethyl-4-amino-3-(trimethylsilanylethyl)phenyl)pyrrolidin-3-yl]trimethylammonium chloride,
3-[1-(5-trimethylsilanylethyl-4-amino-3-(trimethylsilanylethyl)phenyl)pyrrolidin-3-yl]-1-methyl-3H-imidazol-1-ium chloride,
1'-(4-aminophenyl)-1-methyl-[1,3']bipyrrolidinyl-1-ium chloride,
1'-(4-amino-3-methylphenyl)-1-methyl-[1,3']bipyrrolidinyl-1-ium chloride,
3-{[1-(4-aminophenyl)pyrrolidin-3-ylcarbamoyl]methyl}-1-methyl-3H-imidazol-1-ium chloride,
3-{[1-(4-amino-3-methylphenyl)pyrrolidin-3-ylcarbamoyl]methyl}-1-methyl-3H-imidazol-1-ium chloride,
3-[1-(4-aminophenyl)pyrrolidin-3-yl]-1-(3-trimethylsilanylpropyl)-3H-imidazol-1-ium chloride, 3-[1-(4-aminophenyl)pyrrolidin-3-yl]-1-(3-trimethylsilanylpropyl)-3H-imidazol-1-ium chloride,

[1-(4-aminophenyl)pyrrolidin-3-yl]ethyldimethylammonium chloride,

[1-(4-aminophenyl)pyrrolidin-3-yl]ethyldimethylammonium iodide,

[1-(4-aminophenyl)pyrrolidin-3-yl]propyldimethylammonium iodide,

[1-(4-aminophenyl)pyrrolidin-3-yl]propyldimethylammonium bromide,

[1-(4-aminophenyl)pyrrolidin-3-yl]propyldimethylammonium methosulfate,

[1-(4-aminophenyl)pyrrolidin-3-yl]butyldimethylammonium iodide,

[1-(4-aminophenyl)pyrrolidin-3-yl]pentyldimethylammonium iodide,

[1-(4-aminophenyl)pyrrolidin-3-yl]hexyldimethylammonium iodide,

[1-(4-aminophenyl)pyrrolidin-3-yl]heptyldimethylammonium iodide,

[1-(4-aminophenyl)pyrrolidin-3-yl]octyldimethylammonium iodide,

[1-(4-aminophenyl)pyrrolidin-3-yl]decyldimethylammonium iodide,

[1-(4-aminophenyl)pyrrolidin-3-yl]hexadecyldimethylammonium iodide,

[1-(4-aminophenyl)pyrrolidin-3-yl]hydroxyethyldimethylammonium chloride, and

[1-(4-aminophenyl)pyrrolidin-3-yl]hydroxyethyldimethylammonium iodide.

17. The dyeing composition as claimed in claim 8, characterized in that the oxidation dye is a heterocyclic oxidation base chosen from pyridines, pyrimidines, pyrazoles, fused pyrazolopyrimidines, pyrazolotriazoles, pyrazolotetrazoles, pyrazolopyridazines, pyrazolothiazoles, pyrazoloimidazoles, pyrazolobenzimidazoles, pyrazoloquinolines, aminopyrrolidines, aminopyrazolines, mono- or diaminotetraquinolines, diamino- or triaminoquinolines, aminoindazoles, diaminouracils, aminoindolenines, hydrazones, julolidine, lilolidine, their derivatives, and their addition salts.

18. The dyeing composition as claimed in claim 17, characterized in that the heterocyclic base is chosen from pyridines, pyrimidines, pyrazoles, and pyrazolopyrimidines.

19. The dyeing composition as claimed in claim 17, characterized in that the heterocyclic base is chosen from 4,5-diaminopyrazoles.

20. The dyeing composition as claimed in claim 8, characterized in that the oxidation dye is a benzene coupler chosen from meta-aminophenols, meta-phenylenediamines, meta-diphenols, and their addition salts.

21. The dyeing composition as claimed in claim 20, characterized in that the benzene coupler is a meta-aminophenol chosen from compounds of following formula (V):

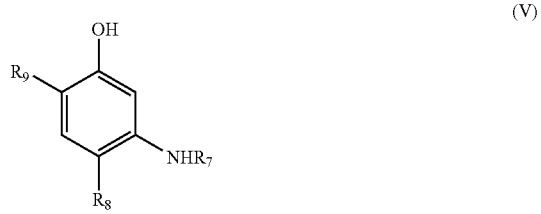

(V)

in which:

$R_7$ represents a hydrogen atom, a $C_1$-$C_4$ alkyl, a $C_1$-$C_4$ monohydroxyalkyl, or a $C_2$-$C_4$ polyhydroxyalkyl group;

$R_8$ represents a hydrogen atom, a $C_1$-$C_4$ alkyl, a $C_1$-$C_4$ alkoxyl group, or a halogen atom chosen from chlorine, bromine, and fluorine; and $R_9$ represents a hydrogen atom, a $C_1$-$C_4$ alkyl, a $C_1$-$C_4$ alkoxyl, a $C_1$-$C_4$ monohydroxyalkyl, a $C_2$-$C_4$ polyhydroxyalkyl, a $C_1$-$C_4$ monohydroxyalkoxyl, or a $C_2$-$C_4$ polyhydroxyalkoxyl group;

and from their addition salts.

22. The dyeing composition as claimed in claim 21, characterized in that the compound of formula (V) is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and their addition salts.

23. The dyeing composition as claimed in claim 20, characterized in that the benzene coupler is a meta-phenylenediamine chosen from compounds of following formula (VI):

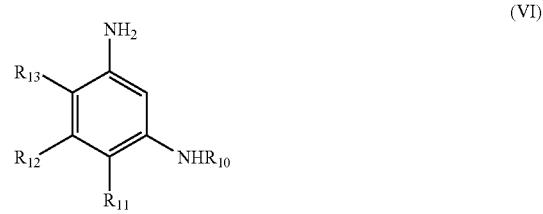

(VI)

in which:

$R_{10}$ represents a hydrogen atom, a $C_1$-$C_4$ alkyl, a $C_1$-$C_4$ monohydroxyalkyl, or a $C_2$-$C_4$ polyhydroxyalkyl group;

$R_{11}$ and $R_{12}$, which are identical or different, represent a hydrogen atom, a $C_1$-$C_4$ alkyl, a $C_1$-$C_4$ monohydroxyalkoxyl, or a $C_2$-$C_4$ polyhydroxyalkoxyl group;

$R_{13}$ represents a hydrogen atom, a $C_1$-$C_4$ alkoxyl, a $C_1$-$C_4$ aminoalkoxyl, a $C_1$-$C_4$ monohydroxyalkoxyl, a $C_2$-$C_4$ polyhydroxyalkoxyl, or a 2,4-diaminophenoxyalkoxyl group;

and from their addition salts.

24. The dyeing composition as claimed in claim 23, characterized in that the compound of formula (VI) is chosen from 2,4-diaminobenzene, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-(methylamino)benzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene, and their addition salts.

25. The dyeing composition as claimed in claim 20, characterized in that the benzene coupler is a meta-diphenol chosen from compounds of following formula (VII):

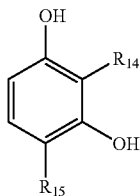

(VII)

in which:
R$_{14}$ and R$_{15}$, which are identical or different, represent a hydrogen atom, a C$_1$-C$_4$ alkyl group, or a halogen atom chosen from chlorine, bromine, and fluorine;
and from their addition salts.

26. The dyeing composition as claimed in claim 25, characterized in that the compound of formula (VII) is chosen from 1,3-dihydroxybenzene, 2-methyl-1,3-dihydroxybenzene, 4-chloro-1,3-dihydroxybenzene, 2-chloro-1,3-dihydroxybenzene, and their addition salts.

27. The dyeing composition as claimed in claim 8, characterized in that the oxidation dye is a heterocyclic coupler chosen from azole heterocyclic couplers, pyridine couplers, thiophenes, indolines, indoles, benzofurans, 8-amino-6-methoxyquinolines, 4-hydroxyquinolones, benzodioxoles, hydroxybenzamides, sesamol and its derivatives, benzomorpholines, and their addition salts.

28. The dyeing composition as claimed in claim 27, characterized in that the heterocyclic coupler is an indole chosen from 6-hydroxyindole, 5,6-hydroxyindole, 4-hydroxyindole, their derivatives, and their addition salts.

29. The dyeing composition as claimed in claim 27, characterized in that the heterocyclic coupler is a benzomorpholine chosen from 6-hydroxybenzomorpholine, 6-aminobenzomorpholine, and their addition salts.

30. The dyeing composition as claimed in claim 8, characterized in that the oxidation dye is a naphthalene coupler chosen from α-naphthol, substituted naphthalenes of following formula (VIII), and their addition salts:

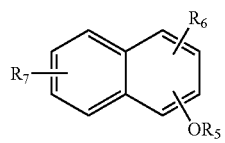

(VIII)

in which:
R$_5$ represents a hydrogen atom or a —CO—R group in which R represents a C$_1$-C$_4$ alkyl group;
R$_6$ represents a hydrogen atom, a hydroxyl group, a C$_1$-C$_4$ alkyl group, or an —SO$_3$H group;
R$_7$ represents a hydrogen atom or a hydroxyl group;
it being understood that at least one of the R$_5$ to R$_7$ groups is other than a hydrogen atom.

31. The dyeing composition as claimed in claim 30, characterized in that the naphthalene coupler is chosen from:
α-naphthol,
1,7-dihydroxynaphthalene,
2,7-dihydroxynaphthalene,
2,5-dihydroxynaphthalene,
2,3-dihydroxynaphthalene,
1-acetoxy-2-methylnaphthalene,
1-hydroxy-2-methylnaphthalene,
1-hydroxy-4-naphthalenesulfonic acid,
and their addition salts.

32. The dyeing composition as claimed in one of claims 1 to 3, characterized in that the concentration of oxidation dye(s) ranges from 0.005 to 15% by weight with respect to the total weight of the composition.

33. The dyeing composition as claimed in one of claims 1 to 3, characterized in that it comprises one or more direct dye(s) chosen from nitrobenzene dyes, azo direct dyes, methine direct dyes, and their addition salts.

34. The dyeing composition as claimed in one of claims 1 to 3, characterized in that it comprises one or more adjuvant(s) chosen from anionic, cationic, nonionic, amphoteric or zwitterionic surface-active agents or their mixtures; nonionic, amphoteric, zwitterionic, anionic or additional cationic polymers, other than the cationic cellulose ethers defined in claim 1, or their mixtures; penetration agents; sequestering agents; fragrances; buffers; dispersing agents; conditioning agents; film-forming agents; ceramides; preservatives; opacifying agents; vitamins, amino acids; oligopeptides; peptides; hydrolyzed or nonhydrolyzed and modified or unmodified proteins; enzymes; branched or unbranched fatty acids and alcohols; animal, vegetable or mineral waxes; hydroxylated organic acids; UV screening agents; antioxidants and agents for combating free radicals; antidandruff agents; seborrhea-regulating agents; soothing agents; mineral, vegetable or animal oils; polyisobutenes and poly(α-olefin)s; pigments; acids; bases; plasticizers; inorganic fillers, pearlescent agents; glitter; antistatic agents and reducing agents.

35. The dyeing composition as claimed in one of claims 1 to 3, characterized in that it comprises at least one thickening agent.

36. The dyeing composition as claimed in one of claims 1 to 3, characterized in that it comprises at least one oxidizing agent chosen from hydrogen peroxide, urea hydrogen peroxide, alkali metal bromates, persalts, peracids, and oxidase enzymes.

37. A method for the oxidation dyeing of keratinous fibers, characterized in that a dyeing composition as defined in any one of claims 1 to 3 is applied to the fibers in the presence of at least one oxidizing agent for a time sufficient to develop the desired color.

38. A multicompartment device, characterized in that it comprises at least one first compartment comprising a dyeing composition as defined in any one of claims 1 to 3 and at least one second compartment comprising at least one oxidizing agent.

39. The use of the composition defined in one of claims 1 to 3 for the dyeing of keratinous fibers, in particular human keratinous fibers.

* * * * *

UNITED STATES PATENT AND TRADEMARK OFFICE
CERTIFICATE OF CORRECTION

| | | |
|---|---|---|
| PATENT NO. | : 8,043,385 B2 | |
| APPLICATION NO. | : 12/671252 | |
| DATED | : October 25, 2011 | |
| INVENTOR(S) | : Marie-Pascale Audousset | |

It is certified that error appears in the above-identified patent and that said Letters Patent is hereby corrected as shown below:

Claim 10, col. 29, line 14, "(ethyl, 62 -hydroxyethyl)" should read -- (ethyl, β-hydroxyethyl) --.

Claim 11, col. 29, line 31, "(p-hydroxyethyl)" should read -- (β-hydroxyethyl) --.

Signed and Sealed this
Fourteenth Day of February, 2012

David J. Kappos
*Director of the United States Patent and Trademark Office*